United States Patent
Elliott et al.

(10) Patent No.: US 6,303,615 B1
(45) Date of Patent: Oct. 16, 2001

(54) 2,3 DISUBSTITUDED-4(3H)-QUINAZOLINONES

(75) Inventors: Mark L. Elliott, Canterbury; Willard M. Welch, Mystic; Bertrand L. Chenard, Waterford, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/180,732

(22) PCT Filed: Feb. 17, 1997

(86) PCT No.: PCT/IB97/00134

§ 371 Date: Nov. 23, 1999

§ 102(e) Date: Nov. 23, 1999

(87) PCT Pub. No.: WO97/43276

PCT Pub. Date: Nov. 20, 1997

Related U.S. Application Data

(60) Provisional application No. 60/017,738, filed on May 15, 1996.

(51) Int. Cl.[7] .................. A61K 31/517; A61P 25/08; C07D 239/74

(52) U.S. Cl. .................. 514/259; 544/284; 544/287; 544/290

(58) Field of Search .................. 544/284, 287, 544/290; 514/259

(56) References Cited

U.S. PATENT DOCUMENTS

| | | | |
|---|---|---|---|
| 3,194,806 | * 7/1965 | Boltze et al. | 260/240 |
| 3,558,610 | * 1/1971 | Brener et al. | 260/240 |
| 5,284,957 | 2/1994 | Huff | 548/110 |
| 5,532,236 | 7/1996 | Jacobsen et al. | 544/60 |
| 5,559,125 | 9/1996 | Kulagowski et al. | 544/128 |

FOREIGN PATENT DOCUMENTS

| | | |
|---|---|---|
| 2114607 | 3/1971 | (DE) . |
| 0056637A1 | 7/1982 | (EP) . |
| 0 056637 | * 7/1982 | (EP) . |
| 0056637B1 | 7/1995 | (EP) . |
| 1298603 | 12/1972 | (IN) . |
| WO9213535 | 8/1992 | (WO) . |
| 92 13535 | * 8/1992 | (WO) . |
| WO9519346 | 7/1995 | (WO) . |
| 95 19346 | * 7/1995 | (WO) . |
| WO9838173 | 2/1998 | (WO) . |

OTHER PUBLICATIONS

Anticonvulsants and MAO inhibitory . . . quinazolones. Shipali etla, Indian J. Exp. Biol. 19(7), 630–633, 1981.*

Sluka, K.A. and Westlund, K.N., Centrally administered non–NMDA but not NMDA receptor antagonists block peripheral knee joint inflammation, Pain. 55 (1993) pp. 217–225.

Westergren, I. and Johansson, B., NBQX, an AMPA antagonist, reduces glutamate–mediated brain edema, Brain Research, 573 (1992) pp. 324–326.

Sheardown, Malcolm J. et al., 2,3–Dihydroxy–6–nitro–7–sulfamoyl–benzo(F)quinoxaline: A Neuroprotectant for Cerebral Ischemia, Science, vol. 247, pp. 571–574.

Le Peillet, Elaine, et al., The non–NMDA antagonists, NBQX and GYKI 52466, protect against cortical and striatal cell loss following transient global ischaemia in the rat, Brain Research, 571 (1992) pp. 115–120.

Shiosaki, Kazumi, and Puttfarcken, Pamela, Emerging Opportunities in Neuroinfalmmatory Mechanisms of Neurodegeneration, Annual Reports in Medicinal Chemistry–30, Chapter 4, pp. 31–38.

Buchan, A., et al. Delayed AMPA receptor blockade reduces cerebral infarction induced by focal ischemia, NeuroReport 2, (1991) 473–476.

Bigge, Christopher F., and Boxer, Peter A., Neuronal Cell Death and Strategies for Neuroprotection, Annual Reports in Medicinal Chemistry–29, Chapter 2, pp. 13–22.

Monn, James A. and Schoepp, Darryle D., Recent Progress in Excitatory Amino Acid Research, Annual Reports in Medicinal Chemistry–29, Chapter 6, pp. 53–64.

Shalaby, Ismail A., et al. (1991) Neuroprotective Effects of the N–Methyl–D–Aspartate Receptor Antagonist, The Journal of Pharmacology and Experimental Therapeutics, vol. 260, No. 2, pp. 925–932.

Rosenberg, Paul A., et al., Jan. (1992) 12(1), Glutamate Uptake Disguises Neurotoxic Potency of Glutamate Agonists in Cerebral Cortex in Dissociated Cell Culture, The Journal of Neuroscience, pp. 56–61.

Koh, Jae Young and Choi, Dennis W., (1987), Quantitative Determination of Glutamate Mediated Cortical Neuronal Injury in Cell Culture by Lactate Dehydrogenase Efflux Assay, Journal of Neuroscience Methods, Journal of Neuroscience Methods, 20, pp. 83–90.

(List continued on next page.)

*Primary Examiner*—Mukund J. Shah
*Assistant Examiner*—Venkataraman Balasubramanian
(74) *Attorney, Agent, or Firm*—Peter C. Richardson; Paul Ginsburg; Kristina L. Konstas

(57) ABSTRACT

The present invention relates to novel 2,3 disubstituted-4 (3H)-quinazolinone compounds of the formula I:

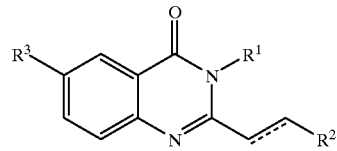

wherein, $R^1$, $R^2$ and $R^3$ are as defined in the specification; and to the pharmaceutically acceptable salts of compounds of formula I, and to pharmaceutical compositions and methods of treating neurodegenerative and CNS-trauma related conditions.

20 Claims, No Drawings

OTHER PUBLICATIONS

Hamill, O.P., et al., (1981), Improved Patch–Clamp Techniques for High–Resolution Current Recording from Cells and Cell–Free Membrane Patches, Pflügers Arch, 391, pp. 85–100.

Kumar, A. et al., (1985) Synthesis and Hypotensive Activity of Trisubstitued Quinazolinones, Dur. J. Med. Chem. 20, No. 1, pp. 95–96.

Badr, M.Z.A. and El–Sherif, H.A.H., (1976), Studies on the Synthesis of 2,3–Disubstituted–4 (3H) Quinazolinone, Egypt. J. Chem, vol. 19, No. 2, pp. 341–346.

Soliman, Raafat, and Somiman, Farid S. G., Oct. 1979, A Facile Synthesis of 2,3–Disubstituted 4–Oxo–3,4–di–hydroquinazolines, Communications, pp. 803–804.

Saksena, S.K., Jul. 1971, Pharmacology Of Some New 4–(3H)–Quinazolinones Part I: Effect On Reproduction, Blood Pressure and Respiration, Indian J Med Res 59, pp. 1109–1112.

Abdel–Bary, E. M. et al., 1974, Evaluation of Some Derivatives of 4–Quinazolones As Antioxidants and Antirads in Rubber, European Polymer Journal, vol. 10, pp. 541–544.

Varma, Rajendra S., Apr. 1974, Potential Biologically Active Agents: VIII. Synthesis of 2–Methyl (and Styryl)–3–Aryl–4–(3H)–Quinazolones, J. Indian Chem. Soc., vol. LII, pp. 344–347.

Varma, R. S. and Singh, S. P., Jul. 1977, Mass Spectra of Some 3–(4–Carbalkoxyphenyl–4–Quinazolones, Indian Journal of Chemistry, vol. 15B, pp. 623–624.

Anwar, M. and Etaiw S. H., 1977, Infrared Absorption Spectra Of Some 4–H–3,1–Benzoxazin–4–Ones and 2,3–Disubstituted–4(3H)–Quinazolinones, Revue Roumaine de Chimic, 22, 8, 1217–1223.

Varma, Rajendra S., et al., 1979, Synthesis of Some 3–(4'–Carbalkoxyphenyl)–7–chlor—2–methylstyryl–4–(3H)–Quinazolinones, Indian J. Chem., vol. 18B, pp. 275–277.

Joshi, Krishna C. and Singh, Virendra K., 1978, Fluorinated Quinazolones. Part VI: Synthesis of some 2–Alkyl 3–Aryl–4(3H)–Quinazolone Derivatives, Egypt J. Chem. vol. 21, No. 6, pp. 451–454.

Abbady, M. A. et al., Jan. 1981, Synthesis of Some New Diarylsulphides and Diarylsulphones Containing Quinazol–4–One Moiety, J. Indian Chem. So., vol. LVIII, pp. 59–61.

Abbady, Mahmoud, A., et al., 1981, Synthesis of Some New Diarylsulphides and Diarylsulphones Containing a Quinazol–4–one Moiety, J. Chem. Tech. Biotechmol, 31, pp. 111–114.

Deodhar, K.D. et al., 1982, Reaction of Schiff Basis: Part I—Convenient Synthesis of 3–Substituted 2–Styryl–4–(3H)–Quinazolinones, India J. Chem., vol. 21 B., p. 67.

Miser, R. S., et al., Synthesis of 2–Substituted Styryl–6–bromo–4–quinazolone 3–(4–Benzhydrazides) as Possible Monoamine Oxidase Inhibitors, J. Heterocyclic Chem., 17, pp. 1337–1338.

Varma, Rajendra S., et al., 1986, "Synthesis of 1–(4–Anilino) Morpholines/Piperidines and Related Compounds as Potential Biodynamic Agents", Indian Drugs, Indian Drugs, 23 (6), p. 345.

Parasharya, P.M. and Parikh, A.R., 1985, Studies on 4(3)–Quinazolone—Part II Preparation and Antibacterial Activity of 2–α, β–Dibromo–Arylethyl α, β–Bisphenyl–Anisyl 4 (3H)–Quinazolones, Acta Ciencia Indica, vol. XI c, No. 1, pp. 71–80.

Jain, Archana and Mukerjee, Arya K., Oct. 1987, One–pot Conversation of 2–Methyl–3,1–benzoxazin–4–one into 3–Substituted–2–styrylquinzolin–4–ones, J. Indian Chem. Soc., vol. LXIV, pp. 645–677.

El–Bayouki, Khairy A. M., Reaction of 2–Styryl–Quinazoline–4–Ones With Tetra–Chloro–o–Benzoquinone: Synthesis of—1,4–Benzodioxins and —4,5–Ortho–Phenylenedioxy–Quinazolone Derivatives of Bactericidal and Fungicidal Activity, Oriental J. Chem vol. 4, No. 1, pp. 84–92.

Gupton, John T. And Shah, Ajit, 1989, A Reinvestigation of the Reaction of Hydrazine Hydrate with 2–Substituted Styryl–4–Quinazolones, Synthetic Communications, 19 (11 & 12), pp. 1875–1883.

Kumar, A., et al., 1985 Synthesis and Hypotensive Activity of Trisubstituted Quinazolinones, Eur. J. Med. Chem., pp. 95–96.

Varma, Rajendar S., Oct. 1985, Synthesis of Heterocyclic Compounds Incorporating 4–Aminostilbene, Indian Journal of Chemistry, vol. 24B, pp. 1039–1042.

Srivatava, Vijai K., 1986, Synthesis of Some Quinazolones, Indian J. Pharm. Sci., 48(5), pp. 133–136.

El–Ansary, A. K., et al., 1979, Synthesis of Some Quinazolone Derivatives as Structurally Related to Certain Sedatives, Hypnotics and Anticonvulsant Agents, Pharmazie 34, H.

Misra, R. S., et al., 1977, Styrylquinazolones As Monoamine Oxidase Inhibitors, Pharmacological Research Communications, vol. 9, No. 5, pp. 437–447.

Misra, R. S., et al., 1979, Anticonvulsant and Monoamine Oxidase Inhibitory Properties of Newer Chlorostrylquinazolones, Pharmacological Research Communications, vol. 11, No. 7, pp. 623–633.

Sammour, A., et al., 1971, Synthesis of Some 4H–3, 1–Benzoxazin–4–Ones and 4–Quinazolones and Their Reaction with Hydrazines, U.A. R. J. Chem., 14, No. 2, pp. 197–205.

Singh, Inder Pal, et al., Jun. 1984, Synthesis and Antiinflammatory Activity of 2–Substituted–phenethyl–3–substituted–phenyl–4(3H)–Quinazolinones, Indian Journal of Chemistry, vol. 23B, pp. 592–594.

El Sabagh, U. L. et al., 1988, Synthesis of Certain 4 (3H) Quinazolinones likely to Possess CNS Depressant and Antimalarial Activities, Egypt. J. Pharm. Sci., vol. 29, No. 1–4, pp. 595–604.

Shukla, S. K., and Agnihotri, A. K., 1984, Antimicrobial Activity of 2,3–Disubstituted 4 (3H)–Qunazolone Derivatives, Indian Journal of Forestry, vol. 7 (2), pp. 151–153.

Misra, R.S., et al., 1981, Synthesis of 2–Styryl–3,6, 8–Trisubstituted Quinazolin 4(3H) Ones as Anti–Inflammatory Agents, J. Chem. Soc. Pak. vol. 3, No. 4., pp. 209–213.

Varma, Rajendra S., et al., Feb. 1981, Synthesis of Some 4–Substituted Phenylmercaptoacetic Acids, Archiv der Pharm, 314, pp. 97–103.

Gaur, V. B., et al., Mar., 1991, 4–(3H)–Quinazolones Part II: 2–Alkyl or Arylaminomethyl Substituted Cinnamyl–3–p–(N–Phenylthiouredosulfo–Phenyl)–4–(3H)– Quinazolones, J. Inst. Chemists(India), vol. 63, pp. 66–68.

Gaur, V. B., et al., Nov. 1991, , 4–(3H)–Quinazolones Part III: 2–Alkyl or Arylaminomethyl Substituted Cinnamyl–3–p–(N–Phenylthiouredosulfo–Phenyl)–4–(3H)– Quinazolones, J. Inst. Chemists(India), vol. 63, pp. 219–220.

Satyanarayana, Mandala, et al., 1985, Electron Impact Mass Spectra of Some 2–Styryl–3–arylquinazolin–4(3H)–ones, Organic Mass Spectrometry, vol. 20, No. 11, 1985, pp. 698–700.

Li, Hui and Buchan, Alastair M., Treatment with an AMPA Antagonist 12 Hours Following Severe Normothermic Forebrain Ischemia Prevents $CA_1$ Neuronal Injury, Journal of Cerebral Blood Flow and Metabolism, 13: pp. 933–939.

Sheardown, Malcolm J., 1993, AMPA, but no NMDA, Receptor Antagonism is Neuroprotective in Gerbil Ischaemia, Even When Delayed 24 h, European Journal of Pharmacology, 236, pp. 347–353.

Xu, Xiao–Jun, et al., 1993, Systemic Excitatory Amino Acid Receptor Antagonists of the α–amino–3–hydroxy–5–methyl–4–isoxazolepropionic acid (AMPA) Receptor and of the N–methyl–D–Aspartate (NMDA) Receptor Relieve Mechanical Hypersensitivity After Transient Spinal Cord Ischemia in Rats, The Journal of Pharmacology and Experimental Therapeutics, vol. 267, No. 1, pp. 140–144.

Bhardwaj, 1984, S. D., Performance of Dioscorea Species Under Sub–Temperate Conditions of Himachal Pradesh, Indian Journal of Forestry, vol. 7 (2), pp. 150–151.

Panse, D. G., Jan. 1982, Synthesis of Laterally Mono– & Di–substituted New Liquid Crystalline Compounds: 2–Chloro–, 3–Methyl– & 2,3–Dimethyl–4'–Substituted–4–(4"–Alkoxybenzoyloxy)–Azobenzenes, Indian J. Chem., vol. 21B, pp. 66–69.

Agnihotri, Anil K., Shukla, Shri K., 1982, Synthesis of New 2,3–Disubsituted 4 (3H)–Quinazolones and Related Products as Potential Antiviral Agents, Arch. Pharm.(Weinheim) 315, pp. 701–706.

Leszkovszky, G., et al., The Pharmacology of Quinazolone Derivatives, Acta Physiologica, XXVII/1, pp. 81–90.

Hisano, Takuzo, et al. 1971, Synthesis and Pharmacological Activities of 2–Heterocyclic Substituted 4(3H)–Quinazolinone Derivatives, Chem. Pharm. Bull. (Tokyo), 19, pp. 2575–2583.

Saskena, S. K., Jul. 1971, Pharmacology of Some New 4–(3H)–Quinazolinones Part I: Effect on Reproduction, Blood Pressure and Respiration, Indian J Med Res 59, 7, pp. 1109–1111.

Sammour, A., et al., 1973, Some Reactions with 2–Styryl–4 H–3, 1–Benzoxazones and 2–Styryl–4 Quinazolones, Egypt J. Chem., 16, No. 3, pp. 215–227.

Tripathi, Shephali, et al., Jul. 1981, Anticonvulsant & MAO Inhibitory Activity of Substituted Quinazolones, Indian Journal of Experimental Biology, vol. 19, pp. 630–633.

Ornstein, Paul L., et al., 1993 (3SR,4aRS,6RS,8aRS)–6–[2–(1H–Tetrazol–5–yl)ethyl] decahydroisoquinoline–3–carboxylic Acid: A Structurally Novel, Systemically Active, Competitive AMPA Receptor Antagonist, J. Med. Chem., 36, pp. 2046–2048.

Watjen, Frank, et al., 1994, NS 257 (1,2,3,6,7,8–Hexahydro–3(Hydroxyimino)–N,N,7–Trimethyl–2–Oxobenzo[2,1–b:3,4–c'] Dipyrrole–5–Sulfonamide)is a Potent, Systemically Active AMPA Receptor Antagonist, Bioorganic & Medicinal Chemistry Letter, vol. 4, No. 2., pp. 371–376.

Watjen, Frank, 1993, Isatin Oximes—A Novel Series of Bioavailable Non–NMDA Antagonists, Bioorganic & Medicinal Chemistry Letters, vol. 3, No. 1, pp. 105–106.

Ohmori, Junya, et al., 1994, 6–(1H–Imidazol–1–yl)–7–nitro–2,3(1H,4H)–quinoxalinedione Hydrochloride (YM90K) and Related Compounds: Structure–Activity Relationships for the AMPA–Type Non–NMDA Receptor, J. Med. Chem., 37, pp. 467–475.

Singh, Buddha Deo and Chaudhury, D.N., 4–Quinazolones Part I. Some Reactions of the Activated Methyl Group in 2–Methyl–3–Phenyl–4–Quinazolone, Jour. Indian Chem. Soc.,45, No. 4., pp. 311–316.

Varma, Rajendra S., et al., 1980, Preparation and Biological Activity of Some 2–Substituted 3–(4' Carboxyphenyl)–7–Nitro–4 (3H)–Quinazolinones, Pol. J. Pharmacol, Pharm., 32, pp. 801–806.

Dwivedi, Chandrdhar, et al., 1980, Correlation Between Monoamine Oxidase Inhibitors and Anticonvulsants, Journal of the National Medical Association, vol. 72, No. 10, pp. 953–955.

Boltz, K.H., et al., Substituted Quinazolinones–(4) as Hypnotic Agents and Anti–Convulsive Agents, Journal not stated, Year 13, vol. 8, pp. 688–701.

Badr, M.Z.A., et al., Oct. 1980, Reactions of 2,3–Disubstituted 4(3H)–Quinazolinones & Related Compounds, Indian J. Chem., vol. 19B, pp. 925–927.

Mass Spectral Studies of Some 2,3–Disubstituted 4(3H)–Quinazolinones, Organic Mass Spectrometry, vol. 18, No. 8, pp. 364–365.

Rawat, Malti, Mar. 1988, Synthesis of Some New 2–Styryl–3–0–Tolyl–4–Quinazolone As Compound of Antifungal Activity, J. Inst. Chemists (India), vol. 60, p. 58.

Ammar, Y. A., 1987, The Synthesis of Some Newer 6,8–Dichloroquinazoline Derivatives As Possible Antibacterial and Antifungal Agents, J. Serb. Chem. Soc. 52(11), pp. 633–639.

Pradhan S. M. et al., Bioequivalence Study of Flunarizine Formulations in Healthy Human Volunteers, Indian Drugs 29 (2), pp. 71–73.

Reddy, A. Malla, et al., Oct. 1990, Synthesis and Antifungal Activity of 2–(4–Aryl–2–pyrazolin–3–yl)–3–aryl–4 (3H)–Quinazolinones, Indian J. Pharm. Sci., 53 (6), pp. 229–232.

Tiwari, S. S, and Pandey, M. P., 1990, Search for New Anthelmintics Part IV Synthesis of Phenoxyacid–Salts of Piperazine Containing Quinazolone Moiety, Acta Ciencia Indica vol. XVI, C, 3, 251, pp. 251–260.

Hisano, Takuzo, et al., 1961, Reaction of 2–Heteroaryl–4(3H)–Quinazolinones with Organic Peracids, J. Chem. Soc., 43, pp. 1173–1182.

Hisano, Takuzo, et al., Am Improved Synthesis of 2–Heteroaryl–3–Phenyl–4(3H)–Quinazolinones, OPPI Briefs, pp. 41–45.

Hisano, Takuzo, et al., 1976, Studies on Organosulfur Compounds. XIV Sulfurations and Oxidations of 2,3–Disubstituted 4(3H)–Quinazolinones, Chem. Pharm. Bull, Chem Pharm. Bull., vol. 24, pp. 2244–2247.

Somasekhara, S. et al., 1971, 3–Aryl–2–isoPropyl and 2–Aryl–3 isoPropyl Derivatives of 4–(3H)–Quinazolinones, The Indian Journal of Pharmacy, vol. 33, No. 1, pp. 26–27.

Zarnowski, T., 1993, 2,3–Dihydroxy–6–Nitro–7–Sulfamoylbenzo(F)Quinoxaline Enhances the Protective Activity of Common Antiepileptic Drugs Against Maximal Electroshock–Induced Seizures in Mice, Neuropharmacology, vol. 32, No. 9, pp. 895–900.

Westergren, Irena, and Johansson, Barbro B., 1992, NBQX, and AMPA Antagonist, Reduces Glutamat–Mediated Brain Edema, Brain Research, 573, pp. 324–326.

Sluka, K.A., and Westlund, K.N., 1993, Centrally Administered non–NMDA But Not NMDA Receptor Antagonist Block Peripheral Knee Joint Inflammation, Pain, 55, pp. 217–225.

Shimizu–Sasamata, M. et al., LXVI–2 The Neuroprotective Action of YM900, A Novel and Potent AMPA Receptor Antagonist, In A Rat Focal Ischemia Model, Journal of Cerebral Blood Flow and Metabolism, Journal of Cerebral Blood Flow and Metabolism, vol. 13, p. 664.

Blackstone, C.D., et al., 1992, Structure and Subunit Composition of AMPA Receptors in the Rat Brain, Society for Neuroscience Abstracts, vol. 18, 1992, pp. 87.

Hamilton, G. S., et al., 1992, Phosphonoethylphenylalanine Derivatives As Novel Antagonists of Non–NMDA Ionotropic Glutamate Receptors, Bioorganic & Medicinal Chemistry Letters, vol. 2, No. 10, pp. 1269–1274.

Rogawski, Michael A., Therapeutic Potential of Excitatory Amino Acid Antagonists: Channel Blockers and 2,3–Benzodiazepines, TIPS, vol. 14, pp. 325–331.

Bigge, Christopher F., et al., Agonists, Antagonists and Modulators of the N–methyl–D–aspartic acid (NMDA) and alpha–amino–3–hydroxy–5–methyl–4–isoxazolepropanoic acid (AMPA) Subtypes of Glutamate Receptors, Current Opinion in Therapeutic Patents, pp. 951–989.

Balasubramanian, V., J. Chem. Soc. Pak. (1981), 3 (4), 209–13.

* cited by examiner

2,3 DISUBSTITUTED-4(3H)-QUINAZOLINONES

This Application claims the benefit of U.S. Provisional Application No. 60/017,738, filed May 15, 1996.

BACKGROUND OF THE INVENTION

The present invention relates to novel compounds of the formula I, described below, and their pharmaceutically acceptable salts, and pharmaceutical compositions and methods of treating neurodegenerative and CNS-trauma related conditions.

The compounds of the invention are potent AMPA receptor antagonists. AMPA receptors are a subspecies of glutamate receptors, identified by their ability to bind α-amino-3-hydroxy-5methyl-4-isoxazolepropionic acid (AMPA), that are implicated as post-synaptic neurotransmitter receptors for excitatory amino acids.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids and their receptors also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinosoitide hydrolysis in the postsynaptic cell. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, and idiopathic and drug-induced Parkinson's Disease. Other neurological conditions, that are caused by glutamate dysfunction, require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic pain, convulsions, retinal neuropathy, tinnitus and tardive dyskinesia. The use of a neuro-protective agent, such as an AMPA receptor antagonist, is believed to be useful in treating these disorders and/or reducing the amount of neurological damage associated with these disorders. The EAA antagonists are also useful as analgesic agents.

Several studies have shown that AMPA receptor antagonists are neuroprotective in focal and global ischemia models. The competitive AMPA receptor antagonist NBQX (2,3-dihydroxy-6-nitro-7-sulfamoylbenzo[f-]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonists GKYI 52466 has been shown to be an effective neuroprotective agent in rat global ischemia models. LaPeillet et al., *Brain Research*, 671, 115 (1992). These studies strongly suggest that the delayed neuronal degeneration in brain ischemia involves glutamate excitotoxicity mediated at least in part by AMPA receptor activation. Thus, AMPA receptor antagonists may prove useful as neuroprotective agents and improve the neurological outcome of cerebral ischemia in humans.

SUMMARY OF THE INVENTION

The present invention relates to a bicyclic compound of the formula

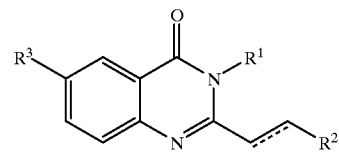

wherein $R^1$ is optionally substituted phenyl of the formula $Ph^1$ or heteroaryl wherein said heteroaryl is selected from the group consisting of pyridin-2-yl, pyridin-3-yl and pyridin-4-yl, wherein said heteroaryl may optionally be substituted on any of the ring carbon atoms capable ot forming an additional bond, up to a maximum of three substituents per ring, with a substituent selected from hydrogen, $(C_1-C_6)$alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN,

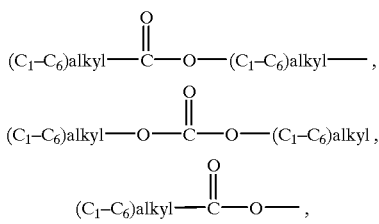

hydroxy, H—C(=O)—, $(C_1-C_6)$alkyl-C(=O)—$(CH_2)_n$—, HO—C(=O)—$(CH_2)_n$—, $(C_1-C_6)$alkyl-O—C(=O)—$(CH_2)_n$—, $NH_2$—C(=O)—$(CH_2)_n$—, $(C_1-C_6)$alkyl-NH—C(=O)—$(CH_2)_n$—, and di$(C_1-C_6)$alkyl-NH—C(=O)—$(CH_2)_n$—;

wherein said $Ph^1$ is a group of the formula

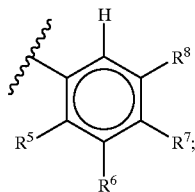

$R^2$ is phenyl of the formula $Ph^2$ or a five or six membered heterocycle, wherein said 6-membered heterocycle has the formula

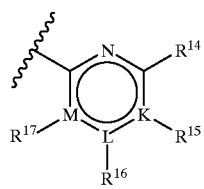

wherein "N" is nitrogen; wherein said ring positions "K", "L" and "M" may be independently selected from carbon or nitrogen, with the proviso that i) only one of "K", "L" or "M" can be nitrogen and ii) when "K", "L" or "M" is nitrogen then its respective $R^{15}$, $R^{16}$ or $R^{17}$ is absent;

wherein said five membered heterocycle has the formula

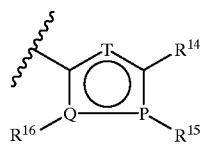

wherein "T" is —CH—, N, NH, O or S; wherein said ring positions "P" and "Q" may be independently selected from carbon, nitrogen, oxygen or sulfur; with the proviso that only one of "P," "Q" or "T" can be oxygen or sulfur and at least one of "P," "Q" or "T" must be a heteroatom;

wherein said $Ph^2$ is a group of the formula

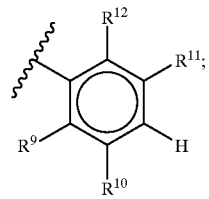

$R^3$ is hydrogen, halo, —CN, —$NO_2$, $CF_3$, $(C_1-C_6)$alkyl or $(C_1-C_6)$alkoxy;

$R^5$ is hydrogen, $(C_1-C_6)$alkyl, halo, $CF_3$, $(C_1-C_6)$alkoxy or $(C_1-C_6)$alkylthiol;

$R^6$ is hydrogen or halo;

$R^7$ is hydrogen or halo;

$R^8$ is hydrogen or halo;

$R^9$ is hydrogen, halo, $CF_3$, $(C_1-C_6)$alkyl optionally substituted with one to three halogen atoms, $(C_1-C_6)$alkoxy optionally substituted with one to three halogen atoms, $(C_1-C_6)$alkylthiol, amino-$(CH_2)_s$—, $(C_1-C_6)$alkyl-NH—$(CH_2)_s$—, di$(C_1-C_6)$alkyl-N—$(CH_2)_s$—, $(C_3-C_7)$cycloalkyl-NH—$(CH_2)_s$—, $H_2N$—(C=O)—$(CH_2)_s$—, $(C_1-C_6)$alkyl-HN—(C=O)—$(CH_2)_s$—, di$(C_1-C_6)$alkyl-N—(C=O)—$(CH_2)_s$—, $(C_3-C_7)$cycloalkyl-NH—(C=O)—$(CH_2)_s$—, $R^{13}O$—$(CH_2)_s$—, $R^{13}O$—(C=O)—$(CH_2)_s$—, H(O=C)—NH—$(CH_2)_s$—, $(C_1-C_6)$alkyl-(O=C)—NH—$(CH_2)_s$—, $(C_1-C_6)$alkyl-(O=C)—

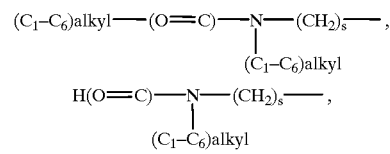

H—(C=O)—$(CH_2)_s$—, $(C_1-C_6)$alkyl-(C=O)—, hydroxy, hydroxy-$(C_1-C_6)$alkyl-, $(C_1-C_6)$alkyl-O—$(C_1-C_6)$alkyl-, and —CN;

$R^{10}$ and $R^{14}$ are selected, independently, from hydrogen, halo, $CF_3$, $(C_1-C_6)$alkyl optionally substituted with one to three halogen atoms, $(C_1-C_6)$alkoxy optionally substituted with one to three halogen atoms, $(C_1-C_6)$alkylthiol, amino-$(CH_2)_p$—, $(C_1-C_6)$alkyl-NH—$(CH_2)_p$, di$(C_1-C_6)$alkyl-N—$(CH_2)_p$—, $(C_3-C_7)$cycloalkyl-NH—$(CH_2)_p$—, amino-$(C_1-C_6)$alkyl-NH—$(CH_2)_p$—, $(C_1-C_6)$alkyl-NH—$(C_1-C_6)$alkyl-NH—$(CH_2)_p$—, di$(C_1-C_6)$alkyl-N—$(C_1-C_6)$alkyl-NH—$(CH_2)_p$—,

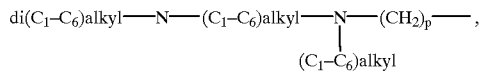

$H_2N$—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$, $(C_3-C_7)$cycloalkyl-NH—(C=O)—$(CH_2)_p$—, $R^{13}O$—$(CH_2)_p$—, $R^{13}O$—(C=O)—$(CH_2)_p$—, H(O=C)—O—, H(O=C)—O—$(C_1-C_6)$alkyl-, H(O=C)—NH—$(CH_2)_p$—, $(C_1-C_6)$alkyl-(O=C)—NH—$(CH_2)_p$—, —CHO, H—(C=O)—$(CH_2)_p$—, $(C_1-C_6)$alkyl-(C=O)—$(CH_2)_p$—,

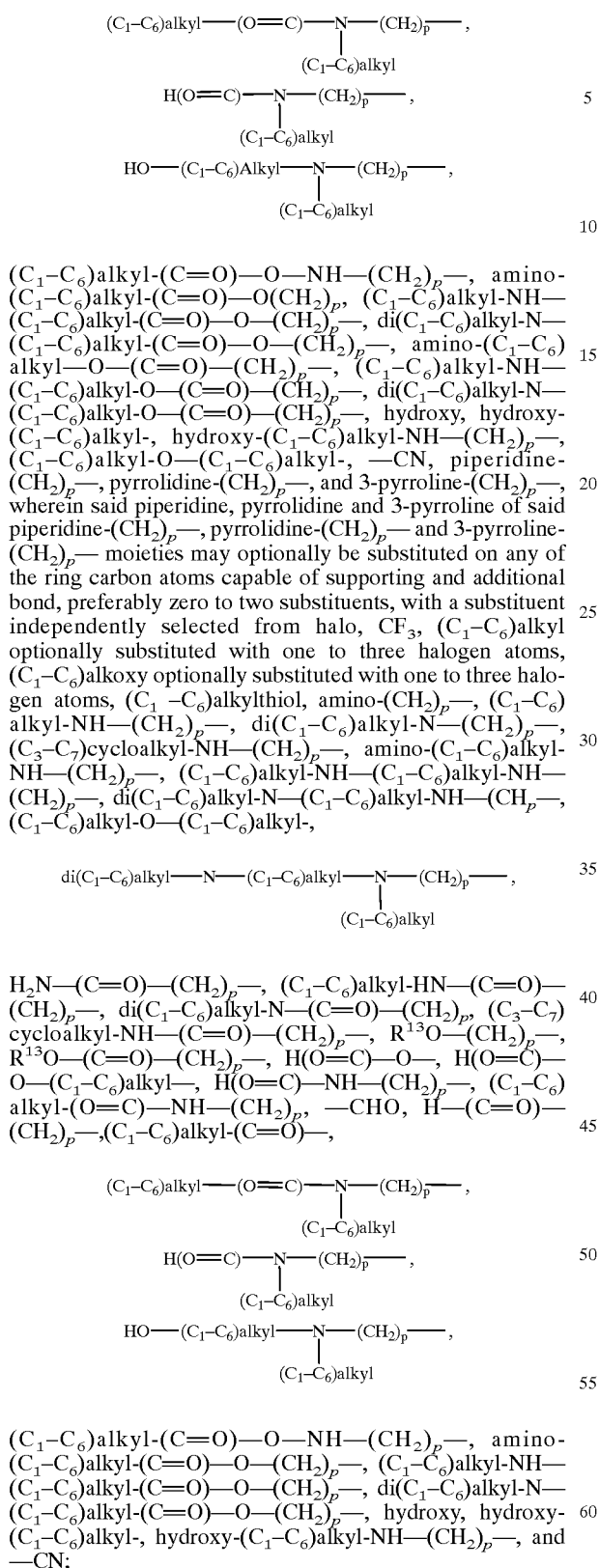

$R^{15}$ is hydrogen, —CN, $(C_1-C_6)$alkyl, halo, $CF_3$, —CHO or $(C_1-C_6)$alkoxy;

$R^{18}$ is hydrogen, —CN, $(C_1-C_6)$alkyl, halo, $CF_3$, —CHO or $(C_1-C_6)$alkoxy, $R^{17}$ is hydrogen, —CN, $(C_1-C_6)$alkyl, amino-$(C_1-C_6)$alkyl-, $(C_1-C_6)$alkyl-NH—$(C_1-C_6)$alkyl-, di$(C_1-C_6)$alkyl-N-$(C_1-C_6)$alkyl-, halo, $CF_3$, —CHO or $(C_1-C_6)$alkoxy;

n is an integer from zero to 3;

each p is independently an integer from zero to 3;

s is an integer from zero to 4;

wherein the dashed bond represented an optional double bond;

with the proviso that: i) when $R^9$ is hydrogen, one of $R^{11}$ and $R^{12}$ is other than hydrogen; ii) when $R^1$ is unsubstituted phenyl and $R^3$ is hydrogen then (a) $R^2$ can not be unsubstituted phenyl, thienyl or furyl or (b) $R^9$ or $R^{12}$ can not be Cl or hydroxy when $R^{10}$ and $R^{11}$ are hydrogen, or (c) $R^{10}$ or $R^{11}$ can not be chloro when $R^9$ and $R^{12}$ are hydrogen; iii) when $R^3$ is hydrogen; $R_6$, $R^7$, and $R^8$ are hydrogen; and $R^5$ is chloro or methyl, then (a) $R^2$ can not be unsubstituted phenyl, thienyl or furyl or (b) $R^{10}$ or $R^{11}$ can not be chloro or (c) $R^9$ or $R^{12}$ can not be hydroxy, methyl or methoxy; iv) when $R^3$ is hydrogen or chloro; $R^5$ is methyl; $R^6$, $R^7$, and $R^8$ are hydrogen; and K, L and M equal carbon, then (a) one of $R^{14}$ through $R^{17}$ must be other than hydrogen or (b) $R^{17}$ must be other than hydrogen or methyl; v) when $R^1$ is unsubstituted pyridin-2-yl and $R^3$ is hydrogen, bromo or iodo then $R^2$ can not be unsubstituted phenyl; vi) when $R^7$ is chloro; $R^5$, $R^6$, and $R^8$ are hydrogen; and $R^3$ is hydrogen, then (a) $R^2$ can not be unsubstituted phenyl, pyridyl, thienyl or furyl or (b) $R^9$ or $R^{12}$ can not be hydroxy when $R^{10}$ and $R^{11}$ are hydrogen; vii) when $R^2$ is unsubstituted phenyl, $R^6$, $R^7$, and $R^8$ are hydrogen, and $R^3$ is hydrogen, then $R^5$ can not be —$CO_2H$; viii) when $R^2$ is unsubstituted pyridin-2-yl, $R^5$ and $R^7$ are hydrogen, and $R^3$ is hydrogen, then $R^6$ or $R^8$ must be other than chloro; ix) when $R^2$ is unsubstituted phenyl, $R^3$ is hydrogen, and $R^5$ and $R^7$ are hydrogen, then one of $R^6$ or $R^8$ must be other than chloro;

and the pharmaceutically acceptable salts of such compounds.

The present invention also relates to the pharmaceutically acceptable acid addition salts of compounds of the formula I. The acids which are used to prepare t he pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

Preferred compounds of formula I are those wherein $R^3$ is fluoro or chloro.

Preferred compounds of formula I wherein $R^1$ is $Ph^1$ are those wherein one of $R^5$, $R^6$, $R^7$ or $R^8$ is fluoro, bromo, chloro, methyl or trifluoromethyl, preferably $R^5$ is fluoro, bromo, chloro, methyl or trifluoromethyl. Most preferred compounds of formula I wherein $R^1$ is $Ph^1$ are those wherein $R^5$ is chloro or methyl.

Preferred compounds of formula I wherein $R^1$ is heteroaryl are those wherein heteroaryl is pyridin-3-yl, optionally substituted with halo, —CN, $CF_3$, or $(C_1–C_6)$alkyl, more preferably chloro or methyl, most preferably substituted at the 2-position.

Preferred compounds of formula I wherein $R^2$ is $Ph^2$ are those wherein $R^9$ is fluoro, chloro, —CN or hydroxy; or $R^{10}$ is —CHO, chloro, fluoro, methyl, $(C_1–C_6)$alkyl-NH—$(CH_2)_p$—, di$(C_1–C_6)$alkyl-N—$(CH_2)_p$—, or cyano. Most preferred compounds of formula I wherein $R^2$ is $Ph^2$ are those wherein $R^9$ is fluoro or —CN; or $R^{10}$ is methyl, $(C_1–C_6)$alkyl-NH—$(CH_2)_p$—, di$(C_1–C_6)$alkyl-N—$(CH_2)_p$—, or cyano.

Preferred compounds of formula I wherein $R^2$ is heteroaryl are those wherein said heteroaryl is either an optionally substituted six-membered heterocycle wherein "K", "L" and "M" are carbon (i.e. pyridin-2-yl), or "K" and "L" are carbon and "M" is nitrogen (i.e. pyrimidin-2-yl), or said heteroaryl is an optionally substituted five membered heterocycle wherein "T" is nitrogen, "P" is sulfur and "Q" is carbon (i.e. 1,3-thiazol4-yl), or "T" is nitrogen or sulfur, "Q" is nitrogen or sulfur and "P" is carbon (i.e. 1,3-thiazol-2-yl) or "T" is oxygen and "P" and "Q" are each carbon (i.e. fur-2-yl).

Preferred compounds of formula I wherein $R^2$ is an optionally substituted six-membered heterocycle wherein "K", "L" and "M" are carbon (i.e. pyridin-2-yl) are those wherein $R^{14}$ is hydrogen, —CHO, chloro, fluoro, methyl, $(C_1–C_6)$alkyl-NH—$(CH_2)_p$—, di$(C_1–C_6)$alkyl-N—$(CH_2)_p$—, or cyano; $R^{17}$ is hydrogen, —CHO, chloro, fluoro, methyl, $(C_1–C_6)$alkyl-NH—$(C_1–C_6)$alkyl, di$(C_1–C_6)$alkyl-N—$(C_1–C_6)$alkyl, or cyano; or $R^{15}$ or $R^{16}$ are independently hydrogen, —CHO, chloro, fluoro, methyl or cyano. Most preferred compounds of formula I wherein $R^2$ is an optionally substituted six-membered heterocycle wherein "K", "L" and "M" are carbon (i.e. pyridin-2-yl) are those wherein $R^{14}$ is hydrogen, —CHO, methyl, $(C_1–C_6)$alkyl-NH— $(CH_2)_p$—, di$(C_1–C_6)$alkyl-N—$(CH_2)_p$—, or cyano.

Preferred compounds of formula I wherein $R^2$ is an optionally substituted five-membered heterocycle wherein "T" is nitrogen, "P" is sulfur and "Q" is carbon (i.e. 1,3-thiazol4-yl) are those wherein $R^{14}$, $R^{15}$ or $R^{16}$ are each independently hydrogen, chloro, fluoro, methyl or cyano.

Preferred compounds of formula I wherein $R^2$ is an optionally substituted five-membered heterocycle wherein "T" is nitrogen or sulfur, "Q" is sulfur or nitrogen and "P" is carbon (i.e. 1,3-thiazol-2-yl) are those wherein $R^{14}$ or $R^{15}$ are independently hydrogen, chloro, fluoro, methyl or cyano.

Specific preferred compounds of the invention include:
3-(2-chloro-phenyl)-2-[2-(5-diethylarninomethyl-2-fluoro-phenyl)-vinyl]-6-fluoro-3H-quinazolin-4-one;
3-(2-chloro-phenyl)-2-[2-(6-diethylaminomethyl-pyridin-2-yl)-vinyl]-6-fuoro-3H-quinazolin-4-one;
3-(2-chloro-phenyl)-2-[2-(4-diethylaminomethyl-pyridin-2-yl)-vinyl]-6-fluoro-3H-quinazolin-4-one;
3-(2-chloro-phenyl)-2-[2-(6-ethylaminomethyl-pyridin-2-yl)-vinyl]-6-fluoro-3H-quinazolin-4-one;
3-(2-bromo-phenyl)-2-[2-(6-diethylaminomethyl-pyridin-2-yl)-vinyl]-6-fluoro-3H-quinazolin-4-one;
3-(2-chloro-phenyl)-6-fluoro-2-[2-(6-methoxymethyl-pyridin-2-yl)-vinyl]-3H-quinazolin-4-one;
6-fluoro-3-(2-methyl-pyridin-3-yl)-2-[2-methyl-thiazoyl-4-yl)-vinyl]-3H-quinazolin-4-one;
3-(2-chloro-phenyl)-6-fluoro-2-[2-(4-methyl-pyrimidine-2-yl)-vinyl]-3H-quinazolin-4-one;
3-(2-chloro-phenyl)-6-fluoro-2-{2-[6-(isopropylarnino-methyl)- pyridin-2-yl]-ethyl}-3H-quinazolin-4-one; and
2-[2-(5-diethylaminomethyl-2-fluoro-phenyl)-vinyl]-6-fluoro-3-(2-methyl-pyridin-3-yl)-3H-quinazolin-4-one.

Other specific compounds of the invention include:
6-Fluoro-3-(3-methyl-pyrazin-2-yl)-2-(2-pyridin-2-yl-vinyl)-3H-quinolin-4-one;
6-Fluoro-3-(4methyl-pyridin-3-yl)-2-(2-pyridin-2-yl-vinyl)-3H-quinazolin-4-one;
3-(2-chloro-phenyl)-6-fluoro-2-(2-pyridin-2-yl-vinyl)-3H-quinazolin-4-one;
3-(2-bromo-phenyl)-2-(2-pyridin-2-yl-vinyl)-3H-quinazolin-4-one;
6-chloro-2-(2-pyridin-2-yl-vinyl)-3-o-tolyl-3H-quinazolin-4-one;
3-(2-chloro-phenyl)-2-[2-(6-methyl-pyridin-2-yl)-vinyl]-3H-quinazolin-4-one;
6-chloro-2-[2-(6-methyl-pyridin-2-yl)-vinyl]-3-o-tolyl-3H-quinazolin-4-one;
3-(2-chloro-phenyl)-6-fluoro-2-(2-pyridin-2-yl-ethyl)-3H-quinazolin-4-one;
6-{2-[3-(2-chloro-phenyl)-6-fluoro-4-oxo-3,4-dihydro-quinazolin-2-yl]-vinyl}-pyridine-2-carbaldehyde;
3-(2-chloro-phenyl)-6-fluoro-2-[2-(6-methylaminomethyl-pyridin-2-yl)-vinyl]-3H-quinazolin-4-one;
N-(6-{2-[3-(2-chloro-phenyl)-6-fluoro-4-oxo-3,4-dihydro-quinazolin-2-yl]-vinyl}-pyridin-2-ylmethyl)-N-methyl-acetamide;
6-{2-[3-(2-chloro-phenyl)-6-fluoro-4-oxo-3,4-dihydro-quinazolin-2-yl]-vinyl}-pyridine-2-carbonitrile;
3-(2-4-fluoro-phenyl)-2-(2-pyridin-2-yl-vinyl)-3H-quinazolin-4-one;
3-(2-bromo-phenyl)-6-fluoro-2-(2-pyridin-2-yl-vinyl)-3H-quinazolin-4-one;
3-(4-bromo-2-chloro-pheny)-6-fluoro-2-(2-pyridin-2-yl-vinyl)-3H-quinazolin-4one;
3-(2-chloro-phenyl)-2-[2-(6-diethylaminomethy-pyridin-2-yl)-vinyl]-3H-quinazolin-4-one;
N-(6-{2-[3-(2-chloro-phenyl)-6-fluoro-4-oxo-3,4-dihydro-quinazolin-2-yl]-vinyl}-pyridin-2-ylmethyl)-N-ethyl-acetamide;
3-(2-chloro-phenyl)-6-fluoro-2-[2-(6-fluoromethyl-pyridin-2-yl)-vinyl]-3H-quinazolin-4-one;
3-(2-chloro-phenyl)-6-fluoro-2-[2-(6-pyrrolidin-1-ylmethyl-pyridin-2-yl)-ethyl]-3H-quinazolin-4-one;
3-(2-chloro-phenyl)-2-[2-(6{[-ethyl-(2-hydroxy-ethyl)-amino]-methyl}-pyridin-2-yl)-vinyl]-6-fluoro-3H-quinazolin-4-one;
3-(2-chloro-phenyl)-6-fluoro-2-{2-[6-(isopropylamino-methyl)-pyridin-2-yl]-vinyl}-3H-quinazolin-4-one;

3-(2-chloro-phenyl)-6-fluoro-2-{2-[6-(2-methyl-piperidin-1-ylmethyl)-pyridin-2-yl]-vinyl}-3H-quinazolin-4-one;

3-(2-chloro-phenyl)-2-[2-(6-ethoxymethyl-pyridin-2-vinyl]-fluoro-3H-quinazolin-4-one;

3-(2-chloro-phenyl)-2-{2-[6-(2,5-dihydro-pyrrol-1-ylmethyl)-pyridin-2-yl]-vinyl}-6-fluoro-3H-quinazolin-4-one;

3-(2-chloro-phenyl)-6-fluoro-2-{2-[6-(4-methyl-piperidin-1-ylmethyl)-pyridin-2-yl]-vinyl}-3H-quinazolin-4-one;

6-bromo-2-[2-(6-methyl-pyridin-2-yl)-vinyl]-o-tolyl-3H-quinazolin-4-one;

6-bromo-2-(2-pyridin-2-yl-vinyl)-3-o-tolyl-3H-quinazolin-4-one;

6-fluoro-3-(2-fluoro-phenyl)-2-(2-pyridin-2-yl-vinyl)-3H-quinazolin-4-one;

1-benzyl-5-(2-methyl-[1,3]dioxolan-2-yl)-2-oxo-2,3-dihydro-1H-indole-3-carboxylic acid (3-phenylcarbamoyl-phenyl)-amide;

3-(2-chloro-phenyl)-6-methyl-2-(2-pyridin-2-yl-vinyl)-3H-quinazolin-4-one;

3-(2-chloro-phenyl)-2-[2-(6-dimethylaminomethyl-pyridin-2-yl)-vinyl]-6-fluoro-3H-quinazolin-4-one;

6-fluoro-3-(2-fluoro-phenyl)-2-[2-(6-methyl-pyridin-2-yl)-vinyl]-3H-quinazolin 3-(2-chloro-phenyl)-2-[2-(6-{[(2-dimethylamino-ethyl)-methyl-amino]-methyl}-pyridin-2-yl)-vinyl]-6-fluoro-3H-quinazolin-4-one;

3-(2-chloro-phenyl)-6-fluoro-2-[2-(6-hydroxymethyl-pyridin-2-yl)-vinyl]-3H-quinazolin-4-one;

acetic acid 6-{2-[3-(2-chloro-phenyl)-6-fluoro-4-oxo-3,4-dihydro-quinazolin-2-yl]-vinyl}-pyridin-2-ylmethyl ester;

6-{-2-[3-(2-bromo-phenyl)-6-fluoro-4-oxo-3,4-dihydro-quinazolin-2-yl]-vinyl}-pyridine-2-carbaldehyde;

3-(2-bromo-phenyl)-2-[2-(6-diethylaminomethyl-pyridin-2-yl)-vinyl]-3H-quinazolin-4-one;

aceticacid 6-{2-[3-(2-bromo-phenyl)-6-fluoro4-oxo-3,4-dihydro-quinazolin-2-yl]-vinyl}-pyridin-2-ylmethyl ester;

diethylamino-acetic acid 6-{2-[3-(2-chloro-phenyl)-6-fluoro-4-oxo-3,4-dihydro-quinazolin-2-yl]-vinyl}-pyridin-2-ylmethyl ester;

3-(2-chloro-phenyl)-2-[2-(6-difluoromethyl-pyridin-2-yl)-vinyl]-6-fluoro-3H-quinazolin-4-one 3-(2-chloro-phenyl)-6-fluoro-2-[2-(6-methoxy-pyridin-2-yl)-vinyl]-3H-quinazolin-4-one 2-{2-[3-(2-chloro-phenyl)-6-fluoro-4-oxo-3,4-dihydro-quinazolin-2-yl]-vinyl}-6-methyl-nicotinonitrile;

2-{2-[3-(2-chloro-phenyl)-6-fluoro-4-oxo-3,4-dihydro-quinazolin-2-yl]-ethyl}-6-methyl-nicotinonitrile;

3-(2-chloro-phenyl)-6-fluoro-2-(2-pyrimidine-2-yl-ethyl)-3H-quinolin-4-one;

3-(2-chloro-phenyl)-2-[2-(4,6-dimethyl-pyrimidine-2-yl)-vinyl]-6-fluoro-3H-quinazolin-4-one;

2-{2-[3-(2-chloro-phenyl)-6-fluoro-4-oxo-3,4-dihydro-quinazolin-2-yl]-vinyl}-nicotinonitrile;

3-(2-chloro-phenyl)-6-fluoro-2-(2-{6-[(3-methyl-butylamino)-methyl]-pyridin-2-yl}-ethyl)-3H-quinazolin-4-one;

2-{2-[3-(2-chloro-phenyl)-6-fluoro-4-oxo-3,4-dihydro-quinazolin-2-yl]-ethyl}-nicotinonitrile;

3-(2-chloro-pyridin-3-yl)-6-fluoro-2-[2-(2-hydroxy-phenyl)-vinyl]-3H-quinazolin-4-one;

2-{2-[6-fluoro-3-(2-methyl-pyridin-3-yl)-4-oxo-3,4dihydro-quinazolin-2-yl)-vinyl}-4-methyl-benzonitrile;

2-[2-(6-chloro-4-oxo-3-o-tolyl-3,4-dihydro-quinazolin-2-yl)-vinyl]-benzonitrile;

2-{2-[3-(2-chloro-phenyl)-6-fluoro-4-oxo-3,4-dihydro-quinazolin-2-yl]-vinyl}-4-methyl-benzonitrile;

3-(2-bromo-phenyl)-6-fluoro-2-[2-(6-hydroxymethyl-pyridin-2-yl)-vinyl]-3H-quinazolin-4-one; and 3-(2-chloro-phenyl)-6fluoro-2-[2-(6-pyrrolidin-1-ylmethyl-pyridin-2-yl)-vinyl]-3H-quinazolin-4-one.

This invention also relates to a pharmaceutical composition for treating or preventing a condition selected from cerebral deficits subsequent to cardiac bypass surgery and grafting, stroke, cerebral- ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising an amount of a compound of formula I effective in treating or preventing such condition and a pharmaceutically acceptable carrier.

This invention also relates to a method of treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising administering to a mammal in need of such treatment or prevention an amount of a compound of formula I effective in treating or preventing such condition.

This invention also relates to a pharmaceutical composition for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising an A MPA receptor antagonizing effective amount of a compound of formula I and a pharmaceutically acceptable carrier.

This invention also relates to a method for treating or preventing a condition selected from cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychopsis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia, in a mammal, comprising administering to a mammal requiring such treatment or prevention an AMPA receptor antagonizing effective amount of a compound of formula I.

The compounds of this invention include all stereoisomers and all optical isomers of compounds of the formula I (e.g., R and S enantiomers), as well as racemic, diastereomeric and other mixtures of such isomers.

The compounds of this invention may contain olefin-like double bonds. When such bonds are present, the compounds of the invention exist as cis and trans configurations and as mixtures thereof.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

Unless otherwise indicated, halo and halogen refer to fluorine, bromine, chlorine or iodine.

DETAILED DESCRIPTION OF THE INVENTION

The compounds of formula I can be prepared according to the methods of Scheme 1. In the reaction Scheme and discussion that follow, K, L, M, P, Q, T, $R^1$, $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $Ph^1$, $Ph^2$, n, m, and p, unless otherwise indicated, are as defined above for formula I.

SCHEME 1

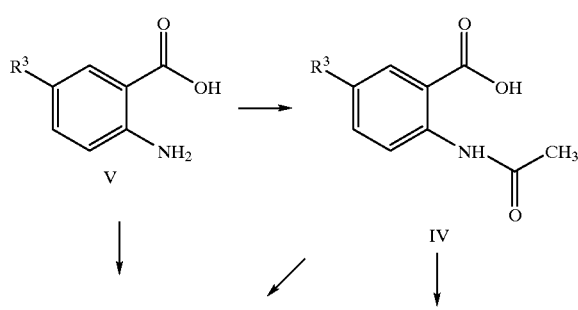

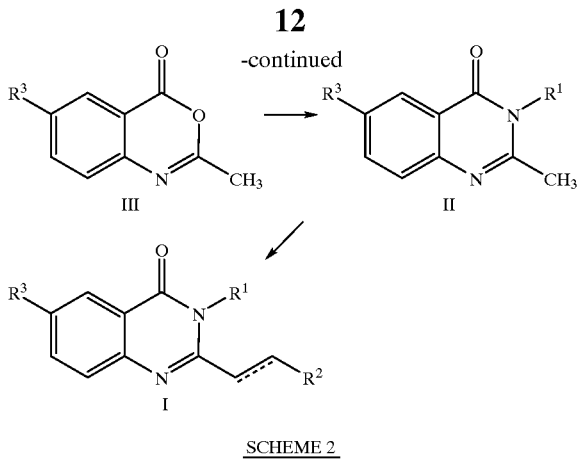

SCHEME 2

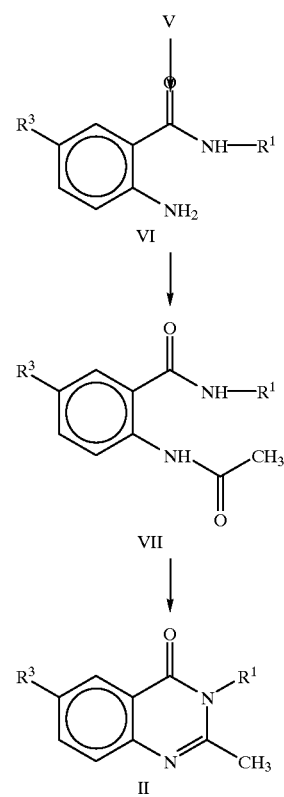

Scheme 1 refers to the preparation of compounds of the formula I from compounds of the formula V. Compounds of the formula V are commercially available or can be prepared by methods well known to those of ordinary skill in the art.

A compound of the formula V can be converted into an acetamide of the formula IV by reaction with acetyl chloride or acetic anhydride in the presence of a base in a reaction inert solvent. Suitable solvents include methylene chloride, dichloroethane, tetrahydrofuran and dioxane, preferably methylene chloride. Suitable bases include trialkylamines such as triethylamine and tributylamine, dimethylaminopyridine and potassium carbonate, preferably triethylamine. The temperature of the aforesaid reaction is in the range from about 0° C. to about 35° C. for about 1 hour to about 10 hours, preferably at about 30° C. for about 3 hours.

The acetamide of the formula IV is cyclized to a compound of the formula III by reaction with a dehydrating agent, in the presence of a catalyst, in dry reaction inert solvent. Suitable dehydrating agents include acetic anhydride, phosphorous pentoxide, dicyclohexylcarbodiimide, and acetyl chloride, preferably acetic anhydride. Suitable catalysts include sodium or potassium acetate, acetic acid, p-toluene sulfonic acid, or boron trifluoride etherate, preferably sodium acetate. Suitable solvents include dioxane, toluene, diglyme or dichloroethane, preferably dioxane. The temperature of the aforesaid reaction is in the range from about 80° C. to about 110° C. for about 1 hour to about 24 hours, preferably at about 100° C. for about 3 to 10 hours.

Alternatively, the compound of formula V can be directly converted into a compound of formula III by reaction with acetic anhydride in the presence of an acid catalyst in a solvent. Suitable acid catalysts include acetic acid, sulfuric acid, or p-toluene sulfonic acid, preferably acetic acid. Suitable solvents include acetic acid, toluene or xylene, preferably acetic acid. The temperature of the aforesaid reaction is from about 20° C. to about 150° C. for about 10 minutes to about 10 hours, preferably at about 120° C. for about 2 to 5 hours.

The compound of formula III, formed by either of the above methods, is reacted with an amine of the formula $R^1NH_2$ in a polar protic solvent in the presence of an acid catalyst to form a compound of the formula II. Suitable acid catalysts include acetic acid, p-toluene sulfonic acid or sulfuric acid, preferably acetic acid. Suitable polar protic solvents include acetic acid, methanol, ethanol or isopropanol, preferably acetic acid. The temperature of the aforesaid reaction is from about 20° C. to about 117° C. for about 1 hour to about 24 hours, preferably at about 117° C. for about 6 hours.

Alternatively, a compound of the formula IV can be directly converted to a compound of the formula II by reaction with a dehydrating agent, an amine of the formula $R^1NH_2$, and a base, in a reaction inert solvent. Suitable dehydrating agents include phosphorous trichloride, phosphorous oxychloride, phosphorous pentachloride or thionyl chloride, preferably phosphorous trichloride. Suitable bases include pyridine, lutidine, dimethyiaminopyridine, triethylamine or N-methyl morpholine, preferably pyridine. Suitable solvents include toluene, cyclohexane, benzene or xylene, preferably toluene. Under some circumstances, when the combined reactants are a liquid, the reaction may be run neat. The temperature of the aforesaid reaction is from about 50° C. to about 150° C. for about 1 hour to about 24 hours, preferably at about 110° C. for about 4 hours.

The compound of formula II is reacted with an aldehyde of the formula $R^2CHO$ in the presence of a catalyst and a dehydrating agent in a suitable solvent to form a compound of the formula I. Suitable catalysts include zinc chloride, sodium acetate, aluminum chloride, tin chloride, or boron trifluoride etherate, preferably zinc chloride or sodium acetate. Suitable dehydrating agents include acetic anhydride, methane sulfonic anhydride, trifluoroacetic anhydride or propionic anhydride, preferably acetic anhydride. Suitable polar solvents include acetic acid, dioxane, dimethoxyethane or propionic acid. The temperature of the aforesaid reaction is from about 60° C. to about 100° C. for about 30 minutes to about 24 hours, preferably at about 100° C. for about 3 hours.

Compounds of the formula I wherein the dashed line represents a single carbon—carbon bond may be prepared by hydrogenating the corresponding compounds wherein the dashed line represents a double carbon—carbon bond, using standard techniques that are well known to those skilled in the art. For example, reduction of the double bond may be effected with hydrogen gas ($H_2$), using catalysts such as palladium on carbon (Pd/C), palladium on barium sulfate ($Pd/BaSO_4$), platinum on carbon (Pt/C), or tris (triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis*, Paul Rylander, Academic Press Inc., San Diego, 1979, pp. 31–63. The following conditions are preferred: Pd on carbon, methanol at 25° C. and 50 psi of hydrogen gas pressure. This method also provides for introduction of hydrogen isotopes (i.e., deuterium, tritium) by replacing $^1H_2$ with $^2H_2$ or $^3H_2$ in the above procedure.

Alternatively, a compound of the formula V can be converted to a compound of the formula II according to the methods described in Scheme 2. The compound of formula II, so formed, can be converted into a compound of formula i according to the methods of Scheme 1. Referring to Scheme 2, a compound of the formula V is reacted with a coupling reagent, an amine of the formula $R^1NH_2$, and a base in a reaction inert solvent to form a compound of the formula VI. Examples of suitable coupling reagents which activate the carboxylic functionality are dicyclohexylcarbodiimide, N-3-dimethylaminopropyl-N'-ethylcarbodiimide, 2-ethoxy-1-ethoxycarbonyl-1,2-dihydroquinoline (EEDQ), carbonyl diimidazole (CDI), and diethylphosphorylcyanide. Suitable bases include dimethylaminopyridine (DMAP), hydroxybenzotriazole (HBT), or triethylamine, preferably dimethylaminopyridine. The coupling is conducted in an inert solvent, preferably an aprotic solvent. Suitable solvents include acetonitrile, dichloromethane, dichloroethane, and dimethylformamide. The preferred solvent is dichloromethane. The temperature of the aforesaid reaction is generally from about −30 to about 80° C., preferably about 0 to about 25° C.

The compound of formula VI is converted into a compound of the formula VII by reaction with acetyl chloride or acetic anhydride in the presence of a base in a reaction inert solvent. Suitable solvents include methylene chloride, tetrahydrofuran and chloroform, preferably methylene chloride. Suitable bases include trialkylamines such as triethylamine and tributylanine, dimethylaminopyridine and potassium carbonate, preferably triethylamine. The temperature of the aforesaid reaction is in the range from about 0° C. to about 35° C. for about 1 hour to about 10 hours, preferably at about 30° C. for about 3 hours.

The compound of formula VII is cyclized to a compound of formula II by reaction with triphenylphosphine, a base, and a dialkyl azodicarboxylate in a reaction inert solvent. Suitable bases include pyridine, triethylamine and 4-dimethylaminopyridine, preferably 4-dimethylaminopyridine. Suitable solvents include dimethylformamide, tetrahydrofuran and dioxane, preferably dioxane. The temperature of the aforesaid reaction is in the range from about 25° C. to about 125° C. for about 1 hour to about 24 hours, preferably at about 100° C. for about 8 to 15 hours. The compound of formula II can be converted into a compound of formula I according to the method described in Scheme 1.

Compounds of formula II can also be made according to the methods described in Miyashita, et al., *Heterocycles*, 42, 2, 691–699 (1996).

Unless indicated otherwise, the pressure of each of the above reactions is not critical. Generally, the reactions will be conducted at a pressure of about one to about three atmospheres, preferably at ambient pressure (about one atmosphere)

When $R^2$ is heteroaryl, one of ordinary skill In the art will understand that heteroaryl is selected from the group consisting of pyridin-2-yl, 1,3-pyrazin-4-yl, 1,4-pyrazin-3-yl, 1,3-pyrazin-2-yl, pyrrol-2yl, 1,3-imidazol-4-yl, 1,3-imidazol-2-yl, 1,3,4-triazol-2-yl, 1,3-oxazol-4-yl, 1,3-oxazol-2-yl, 1,3-thiazol-2-yl, 1,3thiazol-2-yl, 1,2,4-oxadiazol-3-yl, 1,2,4oxadiazol-5-yl, fur-2-yl, 1,3-oxazol-5-yl, and 1,3,4-oxadiazol-2-yl, wherein said heteroaryl may optionally be substituted on any of the atoms capable of forming an additional bond, up to a maximum of three substituents.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate i.,e., 1,1'-methylene-bis-(2-hydroxy-3-naphthoate)] salts.

Those compounds of the formula I which are acidic in nature are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful for the treatment of neurodegenerative and CNS-trauma related conditions and are potent AMPA receptor antagonists. The active compounds of the invention may therefore be used in the treatment or prevention of cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, epilepsy, AIDS-induced demential, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, or tardive dyskinesia.

The in vitro and in vivo activity of the compounds of the invention for AMPA receptor antagonism can be determined by methods available to one of ordinary skill in the art. One method for determining the activity of the compounds of the invention is by inhibition of pentylenetetrazol (PTZ)-induced seizures. Another method for determining the activity of the compounds of the invention is by blockage of AMPA receptor activation-induced $^{45}Ca^{2+}$ uptake.

One specific method for determining the activity of the compounds of the invention for inhibition of pentylenetetrazol (PTZ)-induced seizures in mice can be determined according to the following procedure. This assay examines the ability of compounds to block seizures and death produced by PTZ. Measures taken are latency to clonic and tonic seizures, and death. $ID_{50}$s are determined based on percent protection.

Male CD-1 mice from Charles River, weighing 14–16 g on arrival and 25–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

Mice are administered the test compounds or vehicle (i.p., s.c., or p.o.) and are placed into plexiglass cages in groups of five. At a predetermined time after these injections, mice are given an injection of PTZ (i.p., 120 mg/kg) and placed into individual plexiglass cages. Measures taken during this five minute test period are: (1) latency to clonic seizures, (2) latency to tonic seizures, and (3) latency to death. Treatment groups are compared to the vehicle-treated group by Kruskal-Wallis Anova and Mann-Whitney U tests (Statview). Percent protection is calculated for each group (number of subjects not showing seizure or death as indicated by a score of 300 secs) at each measure. $ID_{50}$'s are determined by probit analysis (Biostat).

Another method for determining the activity of the compounds is to determine the effect of the compounds on motor coordination in mice. This activity can be determined according to the following procedure.

Male CD-1 mice from Charies River, weighing 14–16 g on arrival and 23–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

The apparatus used in these studies consists of a group of five 13.34×13.34 cm wire mesh squares suspended on 11.43 cm steel poles connected to a 165.1 cm pole which is elevated 38.1 cm above the lab bench. These wire mesh squares can be turned upside-down.

Mice are administered test compounds or vehicle (i.p., s.c., or p.o) and are placed into plexiglass cages in groups of five. At a predetermined time after these injections, mice are placed on top of the wire mesh squares and flipped so that they are suspended upside-down. During the one minute test, mice are rated 0 it they fall off the screen,m 1 if they hang on upside-down, or 2 If they climb up onto the top. Treatment groups are compared to the vehicle-treated group with Kruskal-Wallis and Mann-Whitney U tests (Statview).

One specific method for determining blockage of AMPA receptor activation-induced $^{45}Ca^{2+}$ uptake is described below.

Neuronal Primary Cultures

Primary cultures of rat cerebellar granule neurons are prepared as described by Parks, T. N., Artman, L. D., Alasti, N., and Nemeth, E. F., Modulation Of N-Methyl-D-Aspartate Receptor-Mediated Increases In Cytosolic Calcium In Cultured Rat Cerebellar Granule Cells, *Brain Res.* 552, 13–22 (1991). According to this method, cerebella are removed from 8 day old CD rats, minced into 1 mm pieces and incubated for 15 minutes at 37° C. in calcium-magnesium free Tyrode's solution containing 0.1% trypsin. The tissue is then triturated using a fine bore Pasteur pipette. The cell suspension is lated onto poly-D-lysine coated 96-well tissue culture plates at $10^5$ cells per well. Medium consists of Minimal Essential Medium (MEM), with Earle's salts, 10% heat inactivated Fetal Bovine Serum, 2 mM L-glutamine, 21 mM glucose, Penicillin-Streptomycin (100 units per ml) and 25 mM KCl. After 24 hours, the medium is replaced with fresh medium containing 10 $\mu$M cytosine arabinoside to inhibit cell division. Cultures should be used at 6–8 DIV.

AMPA Receptor Activation-induced $^{45}Ca^{2+}$ Uptake

The effects of drugs on AMPA receptor activation-induced $^{45}Ca^{2+}$ uptake can be examined in rat cerebellar granule cell cultures. Cultures in 96 well plates are preincubated for approximately 3 hours in serum free medium and then for 10 minutes in a $Mg^{2+}$-free balanced salt solution (in mM: 120 NaCl, 5 KCl, 0.33 $NaH_2PO_4$ 1.8 $CaCl_2$, 22.0 glucose and 10.0 HEPES at pH 7.4) containing 0.5 mM DTT, 10 uM glycine and drugs at 2× final concentration. The reaction is started by rapid addition of an equal volume of the balanced salt solution containing 100 $\mu$m of the AMPA receptor agonist kainic acid and $^{45}Ca^{2+}$ (final specific activity 250 Ci/mmol). After 10 minutes at 25° C., the reaction is stopped by aspirating the $^{45}Ca^{2+}$-containing solution and washing the cells 5× in an ice cold balanced salt solution containing no added calcium and 0.5 mM EDTA. Cells are then lysed by overnight incubation in 0.1% Triton-X100 and radioactivity in the lysate is then determined. All of the compounds of the invention, that were tested, had $IC_{50}$s of less than 5 $\mu$M.

The compositions of the present Invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous), transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Uquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., ethyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 50 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. NMR data are reported in parts per million ($\delta$) and are referenced to the deuterium lock signal from the sample solvent. Unless otherwise stated, all mass spectrum were performed using chemical impact conditions. Ambient or room temperature refers to 20–25° C.

EXAMPLE 1

3-(2-Chloro-phenyl)-6-fluoro-2-(2-pyridin-2-yl-ethyl)-3H-auinazolin-4-one Hydrochloride A solution of 1.00 gram (2.65 mmol) of 3-(2-Chloro-phenyl)-6-fluoro-2-(2-pyridin-2-yl-vinyl)-3H-quinazolin-4-one in about 100 mL of ethyl acetate was treated with 0.5 gram of 10% Pd/C and the resulting mixture was hydrogenated at about 2 cm of Hg for two hours at which time uptake of hydrogen had ceased. The catalyst was filtered off with the aid of supercel (filteraid) and the ethyl acetated was removed by evaporation. The residues were dissovived in diethyl ether and treated with excess of a solution of HCl gas in diethyl ether. The product precipitated immediately and was allowed to stir for 3 hours at which time it was separated by filtration and dried in a steam of dry nitrogen. The product was 1.15 g (100%) of 3-(2-chloro-phenyl)-6-fluoro-2-(2-pyridin-2-yl-ethyl)-3H-quinazolin-4-one hydrochloride, an amorphous white solid.

EXAMPLE 2

3-(2-Chlorophenyl)-2-[2-(6-diethylaminomethylDvridin-2-yl)-vinyl-6-fluoro-3H-quinazolin-4-one Method A 6-Fluoro-2-methylquinoxalin-4-one A solution of 12.95 9 (70.0 mmol) of 2-nitro-5-fluorobenzoic acid in 200 mL of glacial acetic acid and 20 mL of acetic anhydride was treated with 0.625 g of 10% palladium on carbon are reduced at an initial pressure of 54.5 psi. Hydrogen uptake was complete after two hours. The catalyst was removed by filtration and the filtrate was heated at reflux for two hours at which time TLC (1:1 hexane/ethyl acetate) indicated that the reaction was complete. The reaction mixture was evaporated to a semicrystalline mass which was broken up in a minimum amount of 2-propanol and stirred in an ice bath for one hour. The crystalline solid was separated by filtration, washed with minimal cold 2-propanol and air dried to give 5.79 g (46%) of the desired product as a brown solid, m.p. 127.5–128.5° C.

A synthesis of 5-fluoro-2-nitrobenzoic acid is described by Slothouwer, J. H., *Recl. Trav. Chim. Pays-Bas.* 33, 336 (1914).

Method B 3-(2-Chlorophenyl)-6-fluoro-2-methyl-4-(3H)-quinazolinone.

A solution of 2.50 9 (14.0 mmol) of 6-fluoro-2-methylquinoxalin-4-one and 1.96 g (15.4 mmol) of 2-chloroaniline in about 20 mL of glacial acetic acid was heated at reflux under a nitrogen atmosphere for 6 hours. Most of the solvent was evaporated from the cooled reaction mixture and the residues were taken up in ethanol and refrigerated. After 6 days in the refrigerator, the formed crystals were filtered off, washed with minimal cold ethanol and air dried to give 1.79 9 (44%) of the product. m.p. 137–138° C.

Method C 6-(2-[3-(2-Chlorophenyl)-6-fluoro-4-oxo-3,4-dihydroquinazolin-2-yl-vinyl)pyridine-2-carbaldehyde A catalytic amount (about 100 mg) of anhydrous zinc chloride was added to a solution of 576 mg (2.0 mmol) of 3(2-chlorophenyl)-6-fluoro-2-methyl-4-(3H)-quinazolinone and 270 mg (2.0 mmol) of 2,6-pyridinedicarboxaldehyde in 20–25 mL of dioxane and 1.0 mL of acetic anhydride. The reaction mixture was heated at reflux under a nitrogen atmosphere for 3 hours until TLC indicated that the starting materials had been consumed. The cooled reaction mixture was poured into water and the mixture was extracted with ethyl acetate. The combined extracts were dried with brine and magnesium sulfate, treated with decolonizing carbon and filtered and the solvent was removed to give the desired product. This was taken up in 2:1 ether/pentane and the crystals were filtered to give 266 mg of the product, 33%, m.p. 247–248° C.

A synthesis of pyridine-2,6-dicarboxaldehyde is described by Papadopoulos, et. al., *J. Org. Chem.*, 31, 615 (1966).

Method D 3-(2-Chlorophenyl)-2-[2-(6-diethylaminomethylpyridin-2-yl)-vinyl-6-fluoro-3H-quinazolin-4-one A solution of 65 mg (0.16 mmol) of 6-{2-[3-(2-chlorophenyl)-6-fluoro-4-oxo-3,4-dihydroquinazolin-2-yl)-vinyl)pyridine-2-carbaldehyde in 10 mL of methylene chloride at room temperature under a nitrogen atmosphere was treated with 3 drops of diethylamine and 73 mg (0.34 mmol) of sodium triacetoxyborohydride. After stirring for 2½ hour at room temperature, the solvent was evaporated and the residues were partitioned between dilute hydrochloric acid and either and stirred for 30 minutes. The ethereal layer was separated and the aqueous was extracted once again with either; the ethereal extracts were discarded. The aqueous acidic solution was adjusted to pH=14 with 10% sodium hydroxide (ice bath cooling) and was then extracted with either twice. The combined ethereal extracted were dried with brine and with magnesium sulfate and the solvent was evaporated. After one attempt to form a mesylate salt, the reworked free base in ethyl acetate was treated with 7.5 mg (0.06 mmol) of maleic acid dissolved in a little ethyl acetate. Crystals formed from the resulting solutions which were filtered and washed with ethyl acetate to give 22 mg of the monomaleate salt, (24%), m.p. 170.5–171.5° C.

EXAMPLES 3–69

Examples 3–69 were made according to methods analogous to those of Example 2.

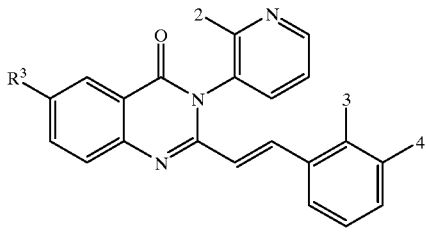

TABLE 1

| Ex | R³ | 2 | 3 | 4 | NMR |
|---|---|---|---|---|---|
| 3 | H | Cl | F | H | (CDCl₃) δ 6.38(1H, d, J=13), 7.00–7.11(2H, m), 7.25–7.34(2H, m), 7.46–7.52(2H, m), 7.77–7.84(3H, m), 8.10(1H, d, J=13), 8.29(1H, d, J=6), 8.61(1H, m). |
| 4 | F | Cl | F | H | (CDCl₃) δ 6.36(1H, d, J=13), 7.00–7.12(2H, m), 7.25–7.33(2H, m), 7.49–7.58(2H, m0, 7.76–7.86(2H, m), 7.91–7.94(1H, d, J=6), 8.08(1H, d, J=13), 8.61(1H, m). |
| 5 | F | CH₃ | F | H | (CDCl₃) δ 2.37(3H, s), 6.35(1H, d, J=13), 7.00–7.10(2H, m), 7.25–7.32(2H, m), 7.37–7.41(1H, m), 7.51–7.58(2H, m), 7.81–7.85(1H, m), 7.91–7.94(1H, d, J=6), 8.06(1H, d, J=13), 8.71(1H, m). |
| 6 | F | Cl | H | —CH₂—N(CH₂CH₃)₂ | (CDCl₃) δ 1.00(6H, t, J=6), 1.98(4H, q, J=6), 3.50(2H, s), 6.29(1H, d, J=13), 7.16–7.66(6H, m), 7.72–7.85(2H, m), 7.92(1H, d, J=6), 8.03 1H, d, J=13), 8.62(1H, m). |
| 7 | F | Cl | H | CHO | (CDCl₃) δ 6.29(1H, d, J=13), 7.47–7.62(4H, m), 7.68–7.96(5H, m), 8.07(1H, d, J=13), 8.63(1H, m), 9.98(1H, s). |
| 8 | H | Cl | H | CHO | (CDCl₃) δ 6.31(1H, d, J=13), 7.48–7.61(5H, m), 7.78–7.84(4H, m), 8.10(1H, d, J=13), 8.30(1H, d, J=6), 8.63(1H, m), 10.00(1H, s). |
| 9 | F | Cl | H | —CH₂OH | (CDCl₃) δ 4.66(2H, s), 6.20(1H, d, J=13), 7.22–7.32(5H, m), 7.50–7.58(2H, m), 7.75–7.83(2H, m), 7.90–7.93(1H, m), 8.02(1H, m, J=13), 8.61(1H, m). |
| 10 | F | Cl | CN | H | (CDCl₃) δ 6.50(1H, d, J=13), 7.39–7.68(6H, m), 7.78–7.95(3H, m), 8.25(1H, d, J=13), 8.62(1H, m). |
| 11 | F | Cl | H | —CH₂—(8-aza-1,4-dioxaspiro[4.5]decane) | (CDCl₃) δ 1.72(4H, broad t), 2.50(4H, broad t), 3.49(2H, s), 3.96(4H, s), 6.21(1H, d, J=13), 7.22–7.35(4H, m), 7.51–7.58(2H, m), 7.77–7.84(2H, m), 7.90–7.94(1H, m), 8.03(1H, d, J=13), 8.64(1H, m). |
| 12 | F | Cl | H | —CH₂—(4-pyrrolidin-1-yl-piperidin-1-yl) | (CDCl₃) δ 1.47–1.61(1H, m), 1.73–2.10(12 H, m), 2.50–2.60(3H, m), 2.77–2.88(1H, m), 3.43(2H, s), 6.70(1H, d, J=13), 7.18–7.33(4H, m), 7.50–7.61(2H, m), 7.74–7.83(2H, m), 7.89–7.96(1H, m), 8.01(1H, d, J=13), 8.67(1H, m). |
| 13 | H | Cl | CN | H | (CDCl₃) δ 6.52(1H, d, J=13), 7.38–7.86(9H, m), 8.27(1H, d, J=13), 8.30(1H, s), 8.61(1H, m). |
| 14 | H | CH₃ | CN | H | (CDCl₃) δ 2.39(3H, s), 6.47(1H, d, J=13), 7.35–7.42(3H, m), 7.49–7.60(3H, m), 7.64–7.67(1H, m), 7.76–7.86(2H, m), 8.29(1H, m), 8.31(1H, d, J=13), 8.70(1H, m). |
| 15 | H | CH₃ | F | H | (CDCl₃) δ 2.38(3H, s), 6.38(1H, d, J=10), 7.00–7.10(2H, m), 7.25–7.32(2H, m), 7.36–7.40(1H, m), 7.47–7.58(2H, m), 8.812(1H, s), 8.11(1H, d, J=10), 8.31(1H, J=6), 8.70(1H, m). |
| 16 | F | Cl | OH | H | (CDCl₃/DMSO-d₆) δ 6.34(1H, d, J=10), 6.55–6.68(2H, m),6.91–7.02(2H, m), 7.32–7.39(2H, m), 7.61–7.79(3H, m), 8.00(1H, d, J=10), 8.41(1H, m). |
| 17 | F | CH₃ | CN | H | (CDCl₃) δ 2.39(3H, s), 6.45(1H, d, J=10), 7.37–7.43(3H, m), 7.49–7.60(3H, m), 7.67(1H, d, J=6), 7.85–7.96(2H, m), 8.28(1H, d, J=10), 8.72(1H, m). |
| 18 | Cl | CH₃ | F | H | (CDCl₃) δ 2.38(3H, s), 6.37(1H, d, J=15), 7.01–7.12(2H, m), 7.24–7.34(2H, m), 7.35(1H, m), 7.57(1H, d, J=6), 7.76(2H, m), 8.12(1H, d, J=15), 8.26(1H, s), 8.73(1H, m). |

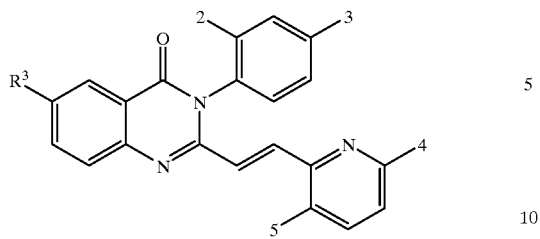
TABLE 2
| Ex | R³ | 2 | 3 | 4 | 5 | NMR |
|---|---|---|---|---|---|---|
| 19 | F | Cl | H | H | H | (CDCl₃) δ 6.84(1H, d, J=15), 7.06–7.14(1H, m), 7.19–7.61(7H, m), 7.70–7.78(1H, m), 7.84–7.89(1H, m), 7.91(1H, d, J=15), 8.42(1H, m). |
| 20 | H | Br | H | H | H | (CDCl₃) δ 6.8979(1H, d, J=15), 7.21–7.82(10H, m), 8.0179(1H, d, J=15), 8.32(1H d, J=7) 8.48(1H, d, J=6). |
| 21 | Cl | CH₃ | H | H | H | (CDCl₃) δ 2.04(3H, s), 6.79(1H, d, J=15), 7.02–7.20(3H, m), 7.24–7.38 (3H, m), 7.46–7.56(1H, m), 7.64(2H, s), 7.88 (1H, d, J=15), 8.16(1H, m), 8.38(1H, m). |
| 22 | H | Cl | H | CH₃ | H | (CDCl₃/DMSO-d₆) δ 2.35 (3H, s), 6.76(1H, d, J=15), 6.97–7.19(3H, m), 7.41–7.58(5H, m), 7.71–7.73(2H, m), 7.89 (1H, d, J=15), 8.21(1H, d, J=7). |
| 23 | Cl | CH₃ | H | CH₃ | H | (CDCl₃) δ 2.10(3H, s), 2.43(3H, s), 6.82(1H, d, J=15), 7.01–7.08(2H, m), 7.19–7.21(1H, m), 7.39–7.51(4H, m), 7.71 (2H, s), 7.96(1H, d, J=15), 8.25(1H, s). |
| 24 | F | Cl | H | H | H | (CDCl₃) δ 3.14–3.42 (2H, m), 3.56–3.69(1H, m), 3.80–3.92(1H, m), 7.50–7.66(4H, m), 7.72–7.84(2H, m), 7.87–8.00(2H, m), 8.09(1H, d, J=6), 8.32(1H, t, J=6), 8.55(1H, d, J=6). |
| 25 | F | Cl | H | CHO | H | (CDCl₃) δ 7.05(1H, d, J=15), 7.41–7.44(1H, m), 7.49–7.57(4H, m), 7.65–7.67(1H, m), 7.81–7.85(2H, m), 7.94–7.97(1H, m), 8.01(1H, d, J=15), 8.05–8.14 (1H, m), 9.84(1H, s). |

TABLE 2-continued

| Ex | R³ | 2 | 3 | 4 | 5 | NMR |
|---|---|---|---|---|---|---|
| 26 | F | Cl | H | —CH₂—NH—CH₃ | H | (CDCl₃) δ 2.67(3H, s), 4.29(2H, ABq, J=15, 23), 6.25(2H, s(maleic acid)), 6.92(1H, d, J=15), 7.23–7.26(2H, m), 7.31–7.33(1H, m), 7.42–7.44(1H, m), 7.49–7.57(3H, m), 7.63–7.65(1H, m), 7.72–7.76 (1H, m), 7.82–7.84(1H, m), 7.90(1H, d, J=15), 7.92–7.96(1H, m). |
| 27 | F | Cl | H | —CH₂—N(CH₃)—C(O)CH₃ | H | (CDCl₃) δ 2.03(3H, s)*, 2.07(3H, s)*, 2.86(3H, s)*, 2.92(3H, s)*, 4.44 (2H, Abq, J=15, 18)*, 4.52(2H, ABq, J=15, 18)*, 6.91–6.96(1H, m), 7.14–7.26(2H, m), 7.39–7.42(1H, m), 7.48–7.67(5H, m), 7.76–7.83 (1H, m), 7.91–7.95(2H, m). *: This compound appears as rotational isomers around the amide carbonyl causing doubling of the acetyl methyl, the N-methyl and the AB quartet of the methylene group. The relative populations at 22° C. are about 65:35. |
| 28 | F | Cl | H | —CH₂—N(CH₂CH₃)₂ | H | (CDCl₃) δ 1.23(6H, t, J=7), 3.01(2H, broad s), 3.09(2H, broad s), 4.22 (2H, d of d, J=14, 17), 6.26(2H, s), 6.88(1H, d, J=15), 7.36–7.41(3H, m), 7.47–7.56(3H, m), 7.62–7.65(1H, m), 7.74–7.83(2H, m), 7.94 (1H, d, J=15), 7.95(1H, m). |
| 29 | F | Cl | H | H | —CH₂—N(CH₂CH₃)₂ | (CDCl₃) δ 1.38(6H, broad s), 3.03 Et2(4H, broad s), 4.31(2H, broad s), 6.97(1H, d, J=15), 7.40–7.67(6H, m), 7.80–7.94(2H, m), 7.94–7.96(1H, m), 8.26 (1H, broad s), 8.40(1H, d, J=15). |
| 30 | F | Cl | H | CN | H | (CDCl₃) δ 6.97(1H, d, J=15), 7.38 7.41(1H, m), 7.47–7.58(5H, m), 7.65–7.67(1H, m), 7.77–7.83(2H, m), 7.90–7.96(2H, m). |
| 31 | H | F | H | H | H | (CDCl₃) δ 7.05(1H, d, J=13), 7.15–7.19(1H, m), 7.29–7.38(4H, m), 7.46–7.58(3H, m), 7.79–7.82(2H, m), 7.98(1H, d, J=13), 8.31(1H, d, J=6), 8.50(1H, m). |
| 32 | F | Br | H | H | H | (CDCl₃) δ 6.87(1H, d, J=13), 7.15–7.21(1H, m), 7.29–7.32(1H, m), 7.39–7.66(5H, m), 7.79–7.84(2H, m), 7.93(1H, d, J=6), 7.96 |

TABLE 2-continued

| Ex | R³ | 2 | 3 | 4 | 5 | NMR |
|----|----|----|----|----|----|-----|
| | | | | | | (1H, d, J=13), 8.50(1H, m). |
| 33 | F | Cl | Br | H | H | (CDCl₃) δ 6.90(1H, d, J=13), 7.17–7.34(3H, m), 7.49–7.58(1H, m), 7.62–7.72(2H, m), 7.79–7.85(2H, m), 7.91–7.94(1H, m), 7.98(1H, d, J=13), 8.53(1H, m). |
| 34 | H | Cl | H | -CH₂-N(CH₂CH₃)₂ | H | (CDCl₃) δ 1.35(6H, broad t), 3.01(4H, broad q), 4.30(2H, broad s), 7.03(1H, d, J=13), 7.56–7.71(6H, m), 7.85–7.99(3H, m), 8.32(1H, d, J=6), 8.76(1H, d, J=6), 8.94(1H, d, J=13). |
| 35 | F | Cl | H | -CH₂-N(CH₂CH₃)(COCH₃) | H | (CDCl₃) δ 7.90–8.00(m, 2H), 7.81(m, 1H), 7.26–7.68(m, 5H), 7.40–7.44(m, 1H), 7.20(m, 2H), 6.86(d, 1H), 4.51(s, 2H), 3.30(q, 2H), 2.09(s, 3H), 1.10(t, 3H). |
| 36 | F | Cl | H | —CH₂F | H | (CDCl₃) δ 7.90–8.00(m, 2H), 7.80–7.86(dd, 1H), 7.62–7.75(m, 2H), 7.48–7.60(m, 3H), 7.35–7.45(m, 2H), 7.25(m, 1H), 6.80(d, 1H), 5.35–5.45(d, 2H). |
| 37 | F | Cl | H | -CH₂-pyrrolidinyl | H | (CDCl₃) δ 7.86–7.87(dd, 1H), 7.66–7.69(dd, 1H), 7.55–7.58(m, 1H), 7.38–7.52(m, 4H), 7.28(m, 1H), 7.13(d, 1H), 7.01(d, 1H), 3.63(s, 2H), 3.28(m, 2H), 2.78(m, 2H), 2.46(b, 4H), 1.72(b, 4H). |
| 38 | F | Cl | H | -CH₂-N(CH₂CH₃)(CH₂CH₂OH) | H | (CDCl₃) δ 7.80–7.96(m, 2H), 7.78–7.82(dd, 1H), 7.57–7.64(m, 2H), 7.46–7.54(m, 3H), 7.37–7.41(m, 1H), 7.15–7.24(m, 2H), 6.88–6.92(d, 1H), 3.68(s, 2H), 3.47–3.49(m, 2H), 2.63(t, 2H), 2.53(q, 2H), 0.99(t, 3H). |
| 39 | F | Cl | H | -CH₂-NH-CH(CH₃)₂ | H | (CDCl₃) δ 7.91–7.96(m, 2H), 7.80–7.83(dd, 1H), 7.71–7.75(t, 1H), 7.62–7.65(m, 1H), 7.49–7.56(m, 3H), 7.43(m, 1H), 7.27–7.30(m, 2H), 6.82–6.86(d, 1H), 6.23(s, 2H), 4.25 4.26(m, 2H), 3.25–3.32(m, 1H), 1.30(m, 6H). |

TABLE 2-continued

| Ex | R³ | 2 | 3 | 4 | 5 | NMR |
|---|---|---|---|---|---|---|
| 40 | F | Cl | H | 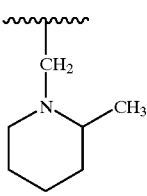 | H | (CDCl₃) δ 7.90–7.97(m, 2H), 7.80(m, 1H), 7.40–7.64(m, 5H), 7.36–7.42(m, 1H), 7.25(m, 1H), 7.14(d, 1H), 6.87–6.91(d, 1H), 3.83(d, 1H), 3.53(d, 1H), 2.69 (m, 1H), 2.00–2.34(m, 2H), 1.2–1.8(m, 6H), 1.05(d, 3H). |
| 41 | F | Cl | H | 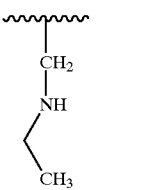 | H | (CDCl₃) δ 7.82–7.96(m, 2H), 7.80(m, 1H), 7.70–7.80(m, 1H), 7.62–7.70(m, 1H), 7.48–7.60(m, 3H), 7.40 (m, 1H), 7.24–7.31(m, 2H), 6.87(d, 1H), 6.24 (s, 2H), 4.28(d, 2H), 3.03(b, 2H), 1.28(t, 3H). |
| 42 | F | Cl | H | 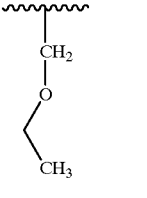 | H | (CDCl₃) δ 7.92–7.98(m, 2H), 7.78–7.81(dd, 1H), 7.6–7.65(m, 2H), 7.48–7.54(m, 3H), 7.38–7.40(m, 1H), 7.33 (d, 1H), 7.18(m, 1H), 6.84(d, 1H), 4.49(s, 2H), 3.60(q, 2H), 1.23(t, 3H). |
| 43 | F | Cl | H | 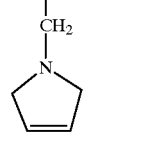 | H | (CDCl₃) δ 7.70–7.90(m, 4H), 7.30–7.70(m, 5H), 7.20–7.30(m, 2H), 6.90(d, 1H), 6.36(b, 2H), 5.80(b, 2H), 4.38(b, 2H), 3.90–4.30(m, 4H). |
| 44 | F | Cl | H | 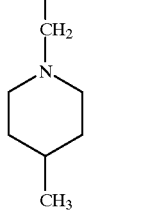 | H | (CDCl₃) δ 7.88–7.97(m, 2H), 7.79(m, 1H), 7.40–7.62(m, 5H), 7.36–7.40(m, 1H), 7.24(m, 1H), 7.14(d, 1H), 6.82–6.86(d, 1H), 3.52(s, 2H), 2.80(m, 2H), 1.97 (m, 2H), 1.56(m, 2H), 1.24(m, 2H), 0.92(d, 3H). |
| 45 | Br | CH₃ | H | CH₃ | H | (CDCl₃) δ 8.43(d, 1H), 7.95–8.00(d, 1H), 7.84–7.87(dd, 1H), 7.65 (d, 1H), 7.43–7.52(m, 4H), 7.20(d, 1H), 7.01–7.09(dd, 2H), 6.80–6.84(d, 1H), 2.43(s, 3H), 2.11(s, 3H). |
| 46 | Br | CH₃ | H | H | H | (CDCl₃) δ 8.30–8.42(m, 2H), 7.88–7.94(d, 1H), 7.78–8.1(dd, 1H), 7.50–7.60(m, 2H), 7.43–7.52(m, 3H), 7.20–7.24(d, 1H), 7.05–7.16(m, 2H), 6.80–6.84(d, 1H), 2.05(s, 3H). |
| 47 | F | F | H | H | H | (CDCl₃) δ 8.48(d, 1H), 7.90–8.00(m, 2H), 7.80 (dd, 1H), 7.45–7.70(m, 3H), 7.30–7.40(m, 4H), 7.15(m, 1H), 7.04(d, 1H). |
| 48 | F | Cl | H | CH₃ | H | (CDCl₃) δ 7.90–8.00(m, |

TABLE 2-continued
| Ex | R³ | 2 | 3 | 4 | 5 | NMR |
|---|---|---|---|---|---|---|
| | | | | | | 2H), 7.80(dd, 1H), 7.65 (m, 1H), 7.55(m, 4H), 7.40(m, 1H), 7.10(d, 1H), 7.05(dd, 1H), 6.85 (d, 1H), 2.42(s, 3H). |
| 49 | CH₃ | Cl | H | H | H | (CDCl₃) δ 8.50(m, 1H), 8.20(d, 1H), 7.95(d, 1H), 7.72(d, 1H), 7.62 (m, 3H), 7.50(m, 2H), 7.38(m, 1H), 7.30(d, 1H), 7.15 dd, 1H), 6.90(d, 1H), 2.50(s, 3H). |
| 50 | F | Cl | H | 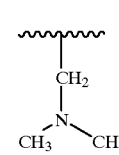 | H | (CDCl₃) δ 7.90–8.00(m, 2H), 7.75(m, 1H), 7.48–7.65(m, 5H), 7.40 (m, 1H), 7.25(d, 1H), 7.18(d, 1H), 6.88(d, 1H), 2.42(s, 3H). |
| 51 | F | F | H | CH₃ | H | (CDCl₃) δ 7.90–8.00(m, 2H), 7.80(dd, 1H), 7.45–7.60(m, 3H), 7.30–7.40(m, 3H), 7.12 (d, 1H), 7.05(d, 1H), 6.96 (d, 1H), 2.45(s, 3H). |
| 52 | F | Cl | H | 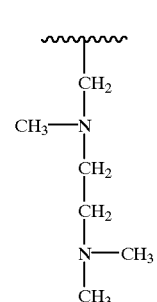 | H | (CDCl₃) δ 7.90–8.00(m, 2H), 7.80(dd, 1H), 7.45–7.65(m, 5H), 7.38 (CH2)2 (m, 1H), 7.30(d, 1H), 7.15(d, 1H), NMe2 6.85(d, 1H), 3.58(s, 2H), 2.48(m, 2H), 2.42(m, 3H), 2.21(s, 3H), 2.20 (s, 6H). |
| 53 | F | Cl | H | 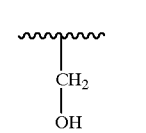 | H | (CDCl₃) δ 7.90–8.00(m, 2H), 7.85(m, 2H), 7.40–7.70(m, 5H), 7.20 (m, 1H), 7.10(d, 1H), 6.95(d, 1H), 4.68(d, 2H). |
| 54 | F | Cl | H | 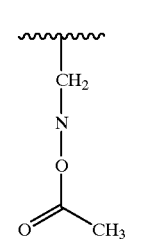 | H | (CDCl₃) δ 7.90–8.00(m, 2H), 7.80(dd, 1H), 7.65 (m, 2H), 7.55(m, 4H), 7.42(m, 1H), 7.24(m, 1H), 6.80(d, 1H), 5.10 (s, 2H), 2.15(s, 3H). |
| 55 | F | Br | H | CHO | H | (CDCl₃) δ 9.35(s, 1H), 7.90–8.07(m, 2H), 7.82 (m, 4H), 7.40–7.62(m, 5H), 7.05(dd, 1H). |
| 56 | F | Br | H | 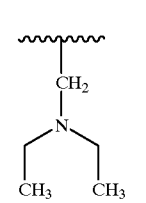 | H | (CDCl₃) (7.90–8.00(m, 2H), 7.80–7.90(m, 2H), 7.30–7.65(m, 6H), 7.15 (d, 1H), 6.85(d, 1H), 3.65(s, 2H), 2.52(q, 4H), 1.04(t, 6H). |

TABLE 2-continued

| Ex | R³ | 2 | 3 | 4 | 5 | NMR |
|---|---|---|---|---|---|---|
| 57 | H | Br | H | CH₂–N(CH₃)(CH₃) wavy bond | H | (CDCl₃) δ 8.32(d, 1H), 7.98(d, 1H), 7.80(m, 3H), 7.44–7.60(m, 3H), 7.36–7.42(m, 3H), 7.33 (d, 1H), 7.17(d, 1H), 6.88 (d, 1H), 3.69(s, 2H), 2.57 (q, 4H), 1.04(t, 3H). |
| 58 | F | Br | H | CH₂–O–C(=O)–CH₃ wavy bond | H | (CDCl₃) δ 7.90–8.00(m, 2H), 7.80(m, 2H), 7.65 (m, 1H), 7.48–7.60(m, 2H), 7.38–7.48(m, 2H), 6.86(d, 1H), 5.08(s, 2H), 2.16(s, 3H). |
| 59 | F | CL | H | CH₂–O–CH₃ wavy bond | H | (CDCl₃) δ 7.90–8.00(m, 2H), 7.78(m, 1H), 7.60–7.68(m, 2H), 7.44–7.56(m, 3H), 7.36–7.42(m, 1H), 7.30(d, 1H0, 7.18(d, 1H), 6.84 (d, 1H), 4.42(s, 2H), 3.40(s, 3H). |
| 60 | F | CL | H | CH₂–O–C(=O)–CH₂–N(CH₂CH₃)(CH₂CH₃) wavy bond | H | (CDCl₃) δ 7.90–8.00(m, 2H), 7.78(m, 1H), 7.60–7.74(m, 2H), 7.46–7.58(m, 3H), 7.40(m, 1H), 7.24(m, 2H), 6.80(d, 1H), 6.26 (s, 2H), 5.21(s, 2H), 3.99(s, 2H), 3.33–3.38 (q, 4H), 1.33–1.36(t, 6H). |
| 61 | | Br | H | CH₂–OH wavy bond | H | (CDCl₃) δ 7.90–8.00(m, 2H), 7.85(m, 2H), 7.40–7.70(m, 5H), 7.23 (m, 1H), 7.07(d, 1H), 6.90(d, 1H), 4.63(d, 2H), 3.62(b, 1H). |
| 62 | F | CL | H | CH₂–N(piperidine) wavy bond | H | (CDCl₃) δ 7.83–7.94(m, 2H), 7.80(m, 1H), 7.70–7.74(m, 1H), 7.61–7.64(m, 1H), 7.41–7.56(m, 3H), 7.40–7.42(m, 1H), 7.30–7.32(m, 2H), 6.85–6.89(d, 1H), 6.22 (s, 2H), 4.24(s, 2H), 3.56(b, 2H), 2.99(b, 2H), 2.01(b, 4H). |

EXAMPLE 63
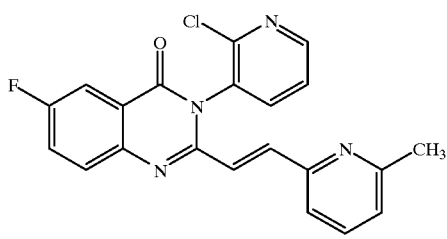
NMR: (CDCl$_3$) δ 2.44 (3H,s), 6.83 (1H, D, J=13), 7.04 (1H, d, J=10), 7.13 (1H, d, J=10), 7.50–7.58 (3H, m), 7.78–7.84 (2H, m), 7.92 (1H, m), 7.96 (1H, d, J=10), 8.61 (1H, m).
EXAMPLE 64
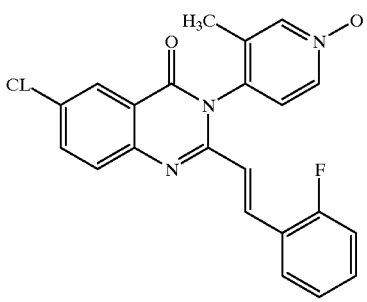
NMR: (CDCl$_3$) δ 2.09 (3H, s), 6.45 (1H, d, J=15), 7.03–7.18 (3H, m), 7.31–7.40 (2H, m), 7.75 (2H, s), 8.14 (1H, d, J=15), 8.22–8.71 (3H, m).
EXAMPLE 65
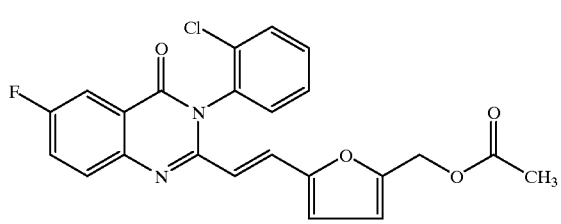
NMR: (CDCl$_3$) (2.05 (3H, s), 4.95 (2H, s), 6.12 (1H, d, J=15), 6.40 (1H, s) 6.50 (1H, s), 7.35–7.37 (1H, m), 7.47–7.55 (3H, m), 7.63–7.65 (1H, m), 7.72–7.75 (2H, m), 7.89–7.92 (1H, m).
EXAMPLE 66
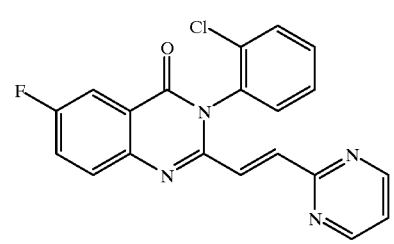
NMR: (CDCl$_3$) (7.10–7.12 (1H, m), 7.15 (1H, d, J=15), 7.38–7.40 (1H, m), 7.48–7.55 (3H, m), 7.63–7.65 (1H, m), 7.81–7.84 (1H, m), 7.92–7.97 (2H, m), 8.64 (2H, s).
EXAMPLE 67
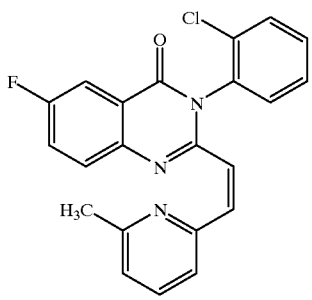
NMR: (CDCl$_3$) (7.98 (dd, 1H), 7.85 (m, 1H, 7.50–7.70 (m, 6H), 7.12 (d, 1H), 7.05 (d H, 6.00(d, 1H), 5.15 (d, 1H), 2.46 (s, 3H).
EXAMPLE 68
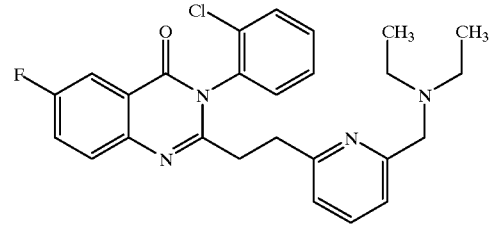
NMR: (CDCl$_3$) (7.90 (dd, 1H), 7.70 (dd, 1H), 7.60(m, 1H), 7.40–7.55 (m, 4H), 7.20–7.35(m, 2H), 7.00 (d, 1H), 3.65 (s, 2H), 3.25 (m, 2H), 2.75 (m, 2H), 2.55 (q, 4H), 1.00 (t, 6H).

EXAMPLE 69

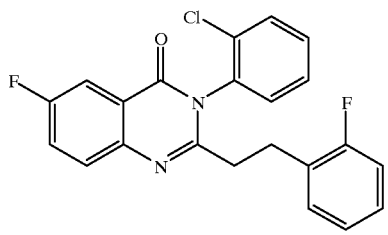

NMR: (CDCl$_3$) δ 2.92 (1H, m), 3.10 (2H, m), 3.42 (1H, m), 6.80–6.88 (1H, m), 6.99–7.06 (1H, m), 7.12–7.20 (2H, m), 7.34–7.42 (1H, m), 7.56–7.72 (4H, m), 7.88–7.96 (1H, m), 8.56 (1H, m).

EXAMPLE 70

6-Fluoro-3-(2-methyl-pyridin-3-yl)-2-[2-(2-methyl-thiazol-4-yl)-vinyl]-3H-quinazolin-4-one mesylate Anhydrous zinc chloride (2.7 g, 20 mmol) was fused with a nitrogen purge in a round bottom flask with an open flame. The reaction vessel was allowed to return to ambient temperature, at which time dioxane (150 mL) was then added. To this mixture was added 6-fluoro-2-methyl-3-(2-methyl-pyridin-3-yl)-3H-quinazolin-4-one (2.6 g, 10 mmol), acetic anhydride (2.8 mL, 30 mmol), and 2-methylthiazole-4-carboxaldehyde (3.7 g, 30 mmol). The reaction was refluxed 2 hours, cooled to ambient temperature, and diluted with water. Sodium carbonate was added until the mixture was basic. The mixture was repeatedly extracted with chloroform. The combined chloroform layer was washed with water and brine and finally dried over sodium sulfate and concentrated to leave a dark residue. This residue treated with methanol and concentrated (effectively azeotroping residual chloroform from the residue) and this process was repeated to leave a brown solid. The solid was triturated with ether (twice), filtered and dried to afford 3.1 g (82%) of 6-fluoro-3-(2-methyl-pyridin-3-yl)-2-[2-(2-methyl-thiazol-4-yl)-vinyl]-3H-quinazolin-4-one as tan solid.

Melting point: 223–224° C.; NMR δ 8.70 (dd, J=1.5, 5 Hz, 1 H), 7.90 (dd partially obscured, J=3 Hz, 1 H), 7.89 (d, J=15 Hz, 1 H), 7.78 (dd, J=5, 9 Hz, 1 H), 7.54 (m, 2 H), 7.39 (dd, J=5, 8 Hz, 1 H), 7.23 (s, 1 H), 6.57 (d, J=15 Hz, 1 H), 2.61 (s, 3 H), 2.36 (s, 3 H). Analysis calculated for C$_{20}$H$_{15}$FN$_4$OS.0.5 H$_2$O: C, 62.06; H, 4.13; N, 14.58. Found: C, 62.39; H, 3.96; N, 14.33.

A sample was taken up in ethyl acetate and treated with 1 N methanesulfonic acid in ethyl acetate to form the mesylate salt. The precipitate was collected, rinsed with ethyl acetate and dried to afford 6-fluoro-3-(2-methyl-pyridin-3-yl)-2-[2-(2-methyl-thiazol-4-yl)-vinyl]-3H-quinazolin-4-one mesylate as a light yellow solid.

Melting point: 230–231° C.; NMR (methanol$_{d4}$) δ 9.01 (dd, J=1.2, 5.8 Hz, 1 H), 8.65 (dd, J=1.3, 8.2 Hz, 1 H), 8.15 (dd, J=5.9, 8.2 Hz, 1 H), 8.00 (d, J=15 Hz, 1 H), 7.88 (sym m, 2 H), 7.71 (m, 2 H), 6.56 (d, J=15 Hz, 1 H), 2.68 (s, 3 H), 2.65 (s, 3 H), 2.62 (s, 3 H). Analysis calculated for C$_{20}$H$_{15}$FN$_4$OS.CH$_3$SO$_3$H.0.75 H$_2$O: C, 51.69; H, 4.20; N, 11.48. Found: C, 51.80; H, 4.18; N, 11.35.

EXAMPLE 71

6-Fluoro-2-[2-(2-methyl-thiazol-4-yl)-vinyl]-3-(2-methyl-phenyl)-3H-quinazolin-4-one Anhydrous zinc chloride (0.136 g, 1.0 mmol) was fused with a nitrogen purge in a round bottom flask with an open flame. The reaction vessel was allowed to return to ambient temperature, then dioxane (10 mL) was added. To this mixture was added 6-fluoro-2-methyl-3-(2-methyl-phenyl)-3H-quinazolin-4-one (0.134 g, 0.5 mmol), acetic anhydride (0.141 mL, 1.5 mmol), and 2-methylthiazole-4-carboxaldehyde (0.191 g, 1.5 mmol). The reaction was refluxed 3.5 h, cooled to ambient temperature, and diluted with water. The mixture was repeatedly extracted with chloroform. The combined chloroform layer was washed with water and brine and finally dried over sodium sulfate and concentrated to leave a dark residue. This residue was triturated with ether, filtered and dried to afford 0.04 g (21%) of 6-fluoro-2-[2-(2-methyl-thiazol-4-yl)-vinyl]-3-(2-methyl-phenyl)-3H-quinazolin-4-one as tan solid.

Melting point: 211–212° C.; NMR δ 7.91 (dd, J=3, 8.3 Hz, 1 H), 7.87 (d, J=15 Hz, 1 H), 7.75 (dd, J=5,9 Hz, 1 H), 7.49 (dt, J=3, 9 Hz, 1 H), 7.42 (sym m, 3 H), 6.61 (d, J=15 Hz, 1 H), 2.60 (s, 3 H), 2.09 (s, 3 H).

EXAMPLE 72

3-(2–chloro-phenyl)-6-fluoro-2-[2-(2-methyl-thiazol-4-yl)-vinyl]-3H-quinazolin-4-one Anhydrous zinc chloride (0.133 g, 0.98 mmol) was fused with a nitrogen purge in a round bottom flask with an open flame. The reaction vessel was allowed to return to ambient temperature, then dioxane (7 mL) was added. To this mixture was added 3-(2-chloro-phenyl)-6-fluoro-2-methyl-3H-quinazolin-4-one (0.14 g, 0.49 mmol), acetic anhydride (0.138 mL, 1.46 mmol), and 2-methylthiazole-4-carboxaldehyde (0.185 g, 1.46 mmol in 4 mL of dioxane). The reaction was refluxed 4 hours, cooled to ambient temperature, and diluted with water. The mixture was repeatedly extracted with chloroform. The combined chloroform layer was washed with water and brine and finally dried over sodium sulfate and concentrated to leave a dark residue. This residue was triturated with ether, filtered and dried to afford 0.16 9 (57%) of 3-(2-chloro-phenyl)-6-fluoro-2-[2-(2-methyl-thiazol-4-yl)-vinyl]-3H-quinazolin-4-one as tan solid.

Melting point: 231–232° C.; NMR δ 7.87–7.84 (m, 2 H), 7.80 (dd, J=4.8, 9 Hz, 1 H), 7.63–7.61 (m, 1 H), 7.52–7.47 (m, 3 H), 7.38–7.35 (m, 1 H), 7.20 (s, 1 H), 6.60 (d, J=15 Hz, 1 H), 2.60 (s, 3 H). Analysis calculated for C$_{20}$H$_{13}$ClFN$_3$OS: C, 60.45; H, 3.27; N, 10.58. Found: C, 59.68; H, 3.17; N, 10.44.

EXAMPLE 73

2-[2-(2-dimethylaminomethyl-thiazol-4-yl)-vinyl]-6-fluoro-3-(2-fluoro-phenyl-3H-quinazolin-4-one Anhydrous zinc chloride (0.106 g, 0.78 mmol) was fused with a nitrogen purge in a round bottom flask with an open flame. The reaction vessel was allowed to return to ambient temperature, then dioxane (6 mL) was added. To this mixture was added 6-fluoro-3-(2-fluoro-phenyl)-2-methyl-3H-quinazolin-4-one (0.108 g, 0.39 mmol), acetic anhydride (0.111 mL, 1.18 mmol), and 2-dimethylaminomethylthiazole-4-carboxaldehyde (0.280 g, 1.18 mmol in 4 mL of dioxane). The reaction was refluxed 4 d, cooled to ambient temperature, and diluted with water. Sodium carbonate was added until the mixture was basic. The mixture was repeatedly extracted with chloroform. The combined chloroform layer was washed with aqueous bisulfite, water and brine and finally dried over sodium sulfate and concentrated to leave a dark residue. This residue was triturated with ether, filtered and dried to afford 0.051 g (31%) of 2-[2-(2-dimethylaminomethyl-thiazol-4-yl)-vinyl]-6-fluoro-3-(2-fluoro-phenyl)-3H-quinazolin-4-one as tan solid.

Melting point: 163–165° C.; NMR δ 7.90 (dd, J=3, 8.5 Hz, 1 H), 7.88 (d, J=s15 Hz, 1 H), 7.76 (dd, J=5, 9 Hz, 1 H), 7.53 (m, 2 H), 7.33 (m, 4 H), 6.74 (d, J=15 Hz, 1 H), 2.48 (br s, 5 H), 1.58 (br s, 3 H). Analysis calculated for $C_{22}H_{18}F_2N_4S \cdot 0.75 H_2O$: C, 60.34; H, 4.46; N, 12.80. Found: C, 60.37; H, 4.38; N, 12.39.

EXAMPLE 74

3-(2-bromo-phenyl)-6-fluoro-2-[2-(2-methyl-thiazol-4-yl)-vinyl]-3H-quinazolin-4-one Anhydrous zinc chloride (0.150 g, 1.1 mmol) was fused with a nitrogen purge in a round bottom flask with an open flame. The reaction vessel was allowed to return to ambient temperature, then dioxane (5 mL) was added. To this mixture was added 3-(2-bromo-phenyl)-6-fluoro-2-methyl-3H-quinazolin-4-one (0.182 g, 0.55 mmol), acetic anhydride (0.156 mL, 1.65 mmol), and 2-methythiazole-4-carboxaldehyde (0.209g, 1.65 mmol in 3 mL of dioxane). The reaction was refluxed 3 h, cooled to ambient temperature, and diluted with water. The mixture was repeatedly extracted with chloroform. The combined chloroform layer was washed with water and brine and finally dried over magnesium sulfate and concentrated to leave a dark residue. This residue was triturated with ether, filtered and dried to afford 0.116 g (52%) of 3-(2-bromo-phenyl)-6-fluoro-2-[2-(2-methyl-thiazol-4-yl)-vinyl]-3H-quinazolin-4-one as tan solid.

Melting point: 233–234° C.; NMR δ 7.96–7.90 (m, 1 H), 7.90 (d, J=15 Hz, 1H), 7.77–7.75 (m, 2 H), 7.55–7.53 (m, 2 H), 7.46–7.38 (m, 2 H), 7.21 (s, 1 H), 6.60 (d, J=15 Hz, 1 H), 2.61 (s, 3 H). Analysis calculated for $C_{20}H_{13}BrFN_3OS \cdot 0.5 H_2O$: C, H, 3.10; N, 9.31. Found: C, 53.07; H, 2.93; N, 9.25.

EXAMPLE 75

3-(2-chloro-phenyl)-2-[2-(2-methyl-thiazol-4-yl)-vinyl]-3H-quinazolin-4-one

Anhydrous zinc chloride (0.136 g, 1.0 mmol) was fused with a nitrogen purge in a round bottom flask with an open flame. The reaction vessel was allowed to return to ambient temperature, then dioxane (10 mL) was added. To this mixture was added 3-(2-chloro-phenyl)-2-methyl-3H-quinazolin-4-one (0.1 35 g, 0.50 mmol), acetic anhydride (0.141 mL, 1.5 mmol), and 2-methylthiazolerboxaldehyde (0.191 g, 1.5 mmol). The reaction was refluxed 3 h, cooled to ambient temperature, and diluted with water. The mixture was repeatedly extracted with chloroform. The combined chloroform layer was washed with water and brine and finally dried over sodium sulfate and concentrated to leave a waxy tan solid. This residue was triturated with ether, filtered and dried to afford 0.139 g (73%) of 3-(2-chloro-phenyl)-2-[2-(2-methyl-thiazol-4-yl)-vinyl]-3H-quinazolin-4-one as tan solid Melting point: 219–221° C.; NMR δ 8.30 (d, J=7.8 Hz, 1 H), 7.91 (d, J=15 Hz, 1 H), 7.78 (m, 2 H), 7.63 (m, 1 H), 7.48 (m, 3 H), 7.38 (m, 1 H), 7.21 (s, 1 H), 6.63 (d, J=15 Hz, 1 H), 2.61 (s, 3 H). Analysis calculated for $C_{20}H_{14}ClN_3OS \cdot 0.5 H_2O$: C, 61.85; H, 3.87; N, 10.82. Found: C, 61.83; H, 3.75; N, 10.55.

EXAMPLE 76–94

The compounds in Table 2 were made by essentially the same procedures as exemplified by Examples 70 through 75.

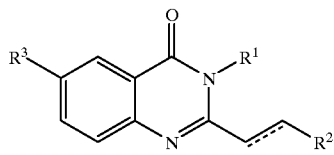

TABLE 2

| Ex | $R_3$ | $R_2$ | $R_1$ | Physical Data |
|---|---|---|---|---|
| 76 | F | 2-methyl-thiazol-4-yl | 2-methyl-phenyl | mp 211–212° C. NMR δ 7.91(dd, J=3, 8.3Hz, 1H), 7.87(d, J=15Hz, 1H), 7.75(dd, J=5, 9Hz, 1H), 7.49(dt, J=3, 9Hz, 1H), 7.42 (sym m, 3H), 6.61(d, J=15Hz, 1H), 2.60(s, 3H), 2.09(s, 3H). |
| 77 | F | 2-methyl-thiazol-4-yl | 2-fluor-ophenyl | mp 228–229° C. NMR δ 7.91(dd, J=3, 8.7Hz, 1H), 7.87(d, J=14.7Hz, 1H), 7.75(dd, J=5, 9Hz, 1H), 7.51(sym m, 2H), 7.33(m, 3H), 7.21(s, 1H), 6.73(d, J=14.7Hz, 1H), 2.61(s, 3H). |
| 78 | Cl | 2-methyl-thiazol-4-yl | 2-methyl-phenyl | mp 195–196° C. NMR δ 8.25(t, J=1.4Hz, 1H), 7.9(d, J=15.Hz, 1H), 7.71(s, 1H), 7.70(s, 1H), 7.43 (sym m, 3H), 7.20(m, 2H), 6.62 (d, J=15Hz, 1H), 2.61(s, 3H), 2.10(s, 3H). |
| 79 | F | 2-dimethyl-amino-methyl-thiazol-4-yl | 2-chlor-ophenyl | mp 190–192° C. NMR δ 7.91(m, 1H), 7.89(d, J=15Hz, 1H), 7.77 (dd, J=5, 9Hz, 1H), 7.62(m, 1H), 7.50(m, 3H), 7.37(m, 2H), 6.59(d, J=15Hz, 1H), 3.76(br s, 2H), 2.38(br s, 6H). |
| 80 | F | 2-dimethyl-amino-methyl-thiazol-4-yl | 2-chlor-opyr-id-3-yl | NMR δ 8.69(br d, J=4.3Hz, 1H), 7.92(m, 2H), 7.78(m, 2H), 7.54 (m, 3H), 6.58(d, J=14.7Hz, 1H), 4.34(br s, 2H), 2.74(br s, 6H). |
| 81 | F | 2-dimethyl-amino-methyl-thiazol-4-yl | 2-meth-ylpyr-id-3-yl | NMR δ 8.67(d, J=4.7Hz, 1H), 7.90(d, J=15Hz, 1H), 7.89(m, 1H), 7.76(dd, J=5, 9Hz, 1H), 7.51 (m, 2H), 7.36(m, 1H), 7.34(s, 1H), 6.55(d, J=15Hz, 1H), 3.70 (s, 2H), 2.34(s, 9H). |
| 82 | F | 2-methyl-oxazol-4-yl | 2-chlor-ophenyl | mp 237° C. NMR δ 7.90(dd, J=8.3Hz, 1H), 7.78(d, J=15Hz, 1H), 7.74(dd, J=4.8, 9Hz, 1H), 7.62(m, 2H), 7.50(m, 3H), 7.36 (m, 1H), 6.44(d, J=15Hz, 1H), 2.38(s, 3H). Analysis calculated for $C_{20}H_{13}ClFN_3O_2 \cdot 0.25H_2O$: C, 62.26; H, 3.50; N, 10.89. Found: C, 61.94; H, 3.46; N, 10.74. |
| 83 | F | 2-methyl-oxazol-4-yl | 2-meth-ylpyr-id-3-yl | mp 223° C. NMR δ 8.69(d, J=3.5Hz, 1H), 7.89(dd, J=3, 8.3Hz, 1H), 7.79(d, J=15Hz, 1H), 7.76 (dd, J=5, 9Hz, 1H), 7.64(s, 1H), 7.53(m, 2H), 7.38(m, 1H), 6.41 (d, J=15Hz, 1H), 2.37(s, 3H), 2.35(s, 3H). |
| 84 | F | 2-methyl-oxazol-4-yl | 2-fluor-ophenyl | mp 232–233° C. NMR δ 7.90(dd, J=3, 8.2Hz, 1H), 7.81(d, J=15Hz, 1H), 7.77(m, 1.H), 7.65 (s, 1H), 7.57–7.47(m, 2H), 7.37–7.24(m, 3H), 6.57(d, J=15Hz, 1H), 2.38 (s, 3H). |
| 85 | F | thiazol-2-yl | 2-chlor-ophenyl | mp 219–220° C. NMR δ 8.13–8.08(d, J=15Hz, 1H), 7.93(dd, J=8.3Hz, 1H), 7.84–7.79(m, 2H), 7.67–7.64(m, 1H), 7.57–7.48(m, 3H), 7.40–7.35(m, 2H), 6.68(d, J=15Hz, 1H). Analysis calculated for $C_{19}H_{11}ClFN_3OS$: C, 59.53; H, 2.87; N, 10.97. Found: C, 59.33; H, 2.91; N, 10.91. |

TABLE 2-continued

| Ex | R₃ | R₂ | R₁ | Physical Data |
|---|---|---|---|---|
| 86 | F | 4-methyl-thiazol-2-yl | 2-chlorophenyl | mp 192–193° C. NMR δ 8.05–8.01(d, J=15Hz, 1H), 7.92(dd, J=8.3Hz, 1H), 7.78(dd, J=4.8, 9Hz, 1H), 7.65–7.62(m, 1H), 7.54–7.49 (m, 3H), 7.38–7.36(m, 1H), 6.88(s, 1H), 6.57(d, J=15Hz, 1H), 2.40(s, 3H). |
| 87 | F | 4,5-dimethyl-thiazol-2-yl | 2-chlorophenyl | mp 218–220° C. NMR δ 7.97(d, J=15Hz, 1H), 7.91(dd, J=3, 8.3Hz, 1H), 7.75(dd, J=5, 9Hz, 1H), 7.62(m, 1H), 7.50(m, 3H), 7.36 (m, 1H), 7.42(d, J=15Hz, 1H), 2.32(s, 3H), 2.28(s, 3H). Analysis calculated for $C_{21}H_{15}ClFN_3OS \cdot 0.5H_2O$: C, 59.93; H, 3.83; N, 9.98. Found: C, 59.82; H, 3.56; N, 9.60. |
| 88 | F | thiazol-2-yl | 2-bromophenyl | mp 236° C. NMR δ 8.10(d, J=15Hz, 1H), 7.94(dd, J=3, 8.3Hz, 1H), 7.83–7.78(m, 3H), 7.58–7.34(m, 5H), 6.66(d, J=15Hz, 1H). Analysis calculated for $C_{19}H_{11}BrFN_3OS$: C, 53.28; H, 2.57; N, 9.82. Found: C, 53.06; H, 2.37; N, 9.76. |
| 89 | F | 4-methyl-thiazol-2-yl | 2-bromophenyl | mp 205° C. NMR δ 8.03(d, J=15Hz, 1H), 7.92(dd, J=2.5, 8Hz, 1H), 7.81–7.75(m, 2H), 7.56–7.48 (m, 2H), 7.43(t, J=7.7Hz, 1H), 7.37(d, J=7.6Hz, 1H), 6.87(s, 1H), 6.54(d, J=15Hz, 1H), 2.40 (s, 3H). Analysis calculated for $C_2OH_{13}BrFN_3OS$: C, 54.19; H, 3.18; N, 9.48. Found: C, 54.05; H, 2.70; N, 9.63. |
| 90 | F | 4-methyl-thiazol-2-yl | 2-methyl-phenyl | mp 198–199° C. NMR δ 8.02(d, J=15Hz, 1H), 7.92(dd, J=3, 8.5Hz, 1H), 7.77(dd, J=5, 9Hz, 1H), 7.53–7.23(m, 4H), 7.17(d, J=7.5Hz, 1H), 6.86(s, 1H), 6.56(d, J=15Hz, 1H), 2.40(s, 3H), 2.09(s, 3H). |
| 91 | F | 4-methyl-thiazol-2-yl | 2-fluorophenyl | mp 219° C. NMR δ 8.02(d, J=15Hz, 1H), 7.91(dd, J=3, 8.3Hz, 1H), 7.77(dd, J=5, 9Hz, 1H), 7.54–7.48(m, 2H), 7.37–7.30(m, 4H) 6.89(s, 1H), 6.70(d, J=15Hz, 1H), 2.40(s, 3H). |
| 92 | F | thiazol-2-yl | 2-chloropyrid-3-yl | mp 195° C. NMR δ 8.61(dd, J=1.7, 5Hz, 1H), 8.10(d, J=15Hz, 1H), 7.92(dd, J=3, 8.2Hz, 1H), 7.82–7.72(m, 3H), 7.57–7.49(m, 2H), 7.37(d, J=3.4Hz, 1H), 6.64 (d, J=15Hz, 1H). |
| 93 | F | thiazol-2-yl | 2-methylpyrid-3-yl | mp 176° C. NMR δ 8.70(dd, J=1.7, 4.7Hz, 1H), 8.09(d, J=15Hz, 1H), 7.91(dd, J=3, 8.3Hz, 1H), 7.89–7.78(m, 2H), 7.55(m, 2H), 7.38–7.34(m, 2H), 6.62(d, J=15Hz, 1H), 2.35(s, 3H). |
| 94 | F | 4-methyl-thiazol-2-yl | 2-methylpyrid-3-yl | mp 178–180° C. NMR δ 8.70(d, J=4Hz, 1H), 8.04(d, J=15Hz, 1H), 7.91(br d, J=8Hz, 1H), 7.79(dd, J=5, 8.7Hz, 1H), 7.55–7.53(m, 2H), 7.40–7.37(m, 1H), 6.91(s, 1H), 6.55(d, J=15Hz, 1H), 2.40(s, 3H), 2.36(s, 3H). |

EXAMPLE 95–113

The compounds in Table 3 were made by essentially the same procedures as exemplified by Example 2.

TABLE 3

| Ex | IUPAC name | NMR |
|---|---|---|
| 95 | 3-(2-Chloro-phenyl)-2-[2-(6-difluoromethyl-pyridin-2-yl)-vinyl]-6-fluoro-3H-quinazolin-4-one | (CDCl₃) δ 6.41(1H, t, J=45), 6.92 (1H, d, J=15), 7.37–7.40(2H, m), 7.43–7. 56(4H, m), 7.60–7.66 (1H, m), 7.73–7.82(2H, m), 7.90 –7.98(2H, m). |
| 96 | 3-(2-Chloro-phenyl)-6-fluoro-2-[2-(6-methoxy-pyridin-2-yl)-vinyl]-3H-quinazolin-4-one | (CDCl₃) δ 3.50(3H, s), 6.53(1H, d, J=1 2), 6.18(1H, d, J=1 2), 6.88 (1H, d, J=15), 7.30–7.48(4H, m), 7.51–7.55(1H, m), 7.69–7.74(2H, m), 7.86(1H, d, J=12). |
| 97 | 2-{2-[3-(2-Chloro-phenyl)-6-fluoro-4-oxo-3,4-dihydro-quinazolin-2-yl]-vinyl}-6-methyl-nicotin-onitrile | (CDCl₃) δ 2.46(3H, s), 7.11(1H, d, J=10), 7.23–7.25(1H, m), 7.38–7.42(1H, m), 7.46–7.64(4H, m), 7.75(1H, d, J=10), 7.83–7.98(2H, m), 8.22(1H, d, J=15). |
| 98 | 3-(2-Chloro-phenyl)-2-[2-(6-diethylamino methyl-pyridin-2-yl)-vinyl]-6-fluoro-3H-quinazolin-4-one | (CDCl₃) δ 1.23(6H, t, J=7), 3.01 (2H, broad s), 3.09(2H, broad s), 4.22(2H, d of d, J=14, 17), 6.26 (2H, s), 6.88(1H,d, J=15), 7.36–7.41(3H, m), 7.47–7.56(3H, m), 7.62–7.65(1H, m), 7.74–7.83(2H, m), 7.94(1H, d, J=15), 7.95(1H, m). |
| 99 | 3-(2-Chloro-phenyl)-2-[2-(6-ethylaminomethyl-pyridin-2-yl)-vinyl]-6-fluoro-3H-quinazolin-4-one | (CDCl₃) δ 1 .26(3H, t, J=8), 2.72 (3H, s), 3.08(2H, broad s), 4.35 (2H, broad s), 7.12–7.21(1H, m), 7.32–7.38(1H, m0, 7.44–7.68 (4H, m)1 7.80–7.90(2H, m), 7.93–8.03(2H, m). |
| 100 | 2-{2-[3-(2-Chloro-phenyl)-6-fluoro-4-oxo-3,4-dihydro-quinazolin-2-yl]-ethyl}-6-methyl-nicotin-onitrile | (CDCl₃) δ 2.44(3H, s), 2.70–2.91 (2H, m), 3.10–3.44(2H, m), 7.09–7.12(1H, m), 7.55–7.77(6H, m), 8.04–8.09(1H, m). |
| 101 | 3-(2-Chloro-phenyl)-6-fluoro-2-(2-pyrimidin-2-yl-ethyl)-3H-quinazolin-4-one | (CDCl₃) δ 2.80–2.98(2H, m), 3.36–3.60(2H, m), 7.02–7.08(1H, m), 7.35–7.48(4H, m), 7.56–7.63(2H, m), 7.84–7.88 1H, m), 8.54–8.60 (1H, d). |
| 102 | 3-(2-Chloro-phenyl)-6-fluoro-2-[2-(4-methyl-pyrimidine-2-yl)-vinyl]-3H-quinazolin-4-one | (CDCl₃) δ 2.45(3H, s), 6.94(1H, m), 7.13(1H, d, J=15), 7.37–7.40 (1H, m), 7.42–7.57(3H, m), 7.59–7.62(1H, m), 7.76–7.80(1H, m), 7.86–8.00(2H, m), 8.44(1H, m). |
| 103 | 3-(2-Chloro-phenyl)-2-[2-(4,6-dimethyl-pyrimidin-2-yl)-vinyl]-6-fluoro-3H-quinazolin-4-one | (CDCl₃) δ 2.40(6H, s), 6.82(1H, s), 7.14(1H, d, J=15), 7.37–7.41(1H, m), 7.46–7.54(4H, m), 7,60–7.64 (1H, m), 7.76–7.80(1H, m), 7.90–8.00(2H, m). |
| 104 | 2-{2-[3-(2-Chloro-phenyl)-6-fluoro-4-oxo-3,4-dihydro-quinazolin-2-yl]-vinyl}-nicotinonitrile | (CDCl₃) δ 7.18–7.29(3H, m), 7.37–7.40(1H, m), 7.44–7.64(4H, m), 7.82–m7.97(3H, m), 8.27(1H, d, J=15), 8.60(1H, m). |
| 105 | 3-(2-Chloro-phenyl)-6-fluoro-2-{2-[6-(isopropylamino-methyl)-pyridin-2-yl]-ethyl}-3H-quinazolin-4-one | (CDCl₃) δ 1.01(6H, d, J=7), 2.70–2.82(2H, m), 3.11–3.28(2H, m), 3.74(2H, s), 6.98(2H, m), 7.24–7.30(1H, m), 7.38–7.50(4H, m), 7.55–7.60(1H, m), 7.65–7.72(1H, m), 7.83–7.90(1H, m). |
| 106 | 3-(2-Chloro-phenyl)-6-fluoro-2-(2-{6-[(3-methyl-butylamino)-methyl]-pyridin-2-yl}-ethyl)-3H-quinazolin-4-one | (CDCl₃) δ 0.86(6H, d, J=12), 1.44–1.64(4H, m), 2.74–2.82(4H, m), 3.12–3.29(2H, m), 3.98(2H, s), 7.08–7.14(2H, m), 7.29–7.34(2H, m), 7.42–7.70 6H, m), 7.86–7.92 (1H, m). |
| 107 | 2-{2-[3-(2-Chloro-phenyl)-6-fluoro-4-oxo-3,4-dihydro-quinazolin-2-yl]-ethyl}-nicotinonitrile | (CDCl₃) δ 3.45–3.60(2H, m), 4.07–4.17(2H, m), 6.82–7.50(5H, m), 7.60–7.65(1H, m), 7.71–7.77(1H, m), 7.83–7.93(2H, m), 8.59–8.64 (1H, m). |

TABLE 3-continued

| Ex | IUPAC name | NMR |
|---|---|---|
| 108 | 3-(2-Chloro-pyridin-3-yl)-6-fluoro-2-[2-(2-hydroxy-phenyl)-vinyl]-3H-quinazolin-4-one | (CDCl$_3$ + DMSO-d6) δ 5.99(1H, d, J=15), 6.16–6.24(1H, m), 6.38 (1H, d, J=10), 6.42–6.66(2H, m), 6.93–7.12(2H, m), 7.23–7.45(3H, m), 7.60(1H, d, J=15), 8.04(1H, m), 9.23(1H, broad s). |
| 109 | 2-{2-[6-Fluoro-3-(2-methyl-pyridin-3-yl)4-oxo-3,4-dihydro-quinazolin-2-yl]-vinyl}4-methyl-benzonitrile | (CDCl$_3$ + DMSO-d6) δ 2.03(3H, s), 2.07(3H, s), 6.15(1H, d, J=15), 6.82–6.94(2H, m), 7.11–7.60(7H, m), 7.91(1H, d, J=15), 8.41(1H, m). |
| 110 | 2-[2-(5-Diethylamino-methyl-2-fluoro-phenyl)-vinyl]-6-fluoro-3-(2-methyl-pyridin-3-yl)-3H-quinazolin-4-one | (CDCl$_3$ + DMSO-d6) δ 1.72(6H, broadened t), 2.76(3H, s), 2.67 (2H, broad q), 3.05(2H, broad q), 3.96(2H, m), 6.40(d, J=15), 6.69–6.78(1H, m), 7.13–7.31(2H, m), 7.48–7.58(2H, m), 7.72–7.80(1H, m), 7.88(1H, d, J=15), 8.05–8.16 (2H, m), 8.44(1H, m). |
| 111 | 2-[2-(6-Chloro-4-oxo-3-o-tolyl-3,4-dihydro-quinazolin-2-yl)-vinyl]-benzonitrile | (CDCl$_3$) δ 2.14(3H, s), 6.52(1H, d, J=15), 7.15–7.54(6H, m), 7.62–7.85(4H, m), 8.24–8.30(2H, m). |
| 112 | 3-(2-Chloro-phenyl)-2-[2-(5-diethylamino methyl-2-fluoro-phenyl)-vinyl]-6-fluoro-3H-quinazolin-4-one | (CDCl$_3$) δ 1.00(6H, t, J=10), 2.50 (4H, q, J=10), 3.52(2H, s), 6.43 (1H, d, J=15), 6.88–6.96(1H, m), 7.20–7.65(9H, m), 7.76–7.83(1H, m), 7.89–7.94(1H, m), 7.99 ,(1H, d, J=15). |
| 113 | 2-{2-[3-(2-Chloro-phenyl)-6-fluoro-4-oxo-3,4-dihydro-quinazolin-2-yl]-vinyl}-4-methyl-benzonitrile | (CDCl$_3$) δ 2.32(3H, s), 6.51(1H, d, J=15), 7.12–7.28(3H, m), 7.36–7.43(1H, m), 7.48–7.59(4H, m), 7.63–7.70(1H, m), 7.81–7.98(2H, m), 8.20(1H, d, J=15). |

What is claimed is:

1. A compound of the formula

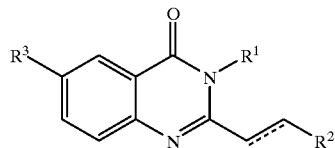

I wherein $R^1$ is optionally substituted phenyl of the formula $Ph^1$ or heteroaryl wherein said heteroaryl is selected from the group consisting of pyridin-2-yl, pyridin-3-yl, and pyridin-4-yl, wherein said heteroaryl may optionally be substituted on any of the ring carbon atoms capable of forming an additional bond, up to a maximum of three substituents per ring, with a substituent selected from hydrogen, $(C_1-C_6)$alkyl, halogen, trefluoromethyl, amino-$(CH_2)_n$—, $(C_1-C_6)$alkylamino-$(CH_2)_n$—, di$(C_1-C_6)$alkyl-amino-$(C_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-C(=O)—O—$(C_1-C_6)$alkyl-, $(C_1-C_6)$alkyl-C(=O)—O—$(C_1-C_6)$alkyl, $(C_1-C_6)$alkyl-C(=O)—O—, hydroxy, H—C(=)—, $(C_1-C_6)$alkyl-C(=O)—$(CH_2)_n$—, HO—C(=O)—$(CH_2)_n$—, $(C_1-C_6)$alkyl-O—C(=O)—$(CH_2)_n$—, $NH_2$—C(=O)—$(CH_2)_n$—, $(C_1-C_6)$alkyl-NH—C(=O)—$(CH_2)_n$—, and di$(C_1-C_6)$alkyl-NH—C(=O)—$(CH_2)_n$—;

wherein said $Ph^1$ is a group of the formula

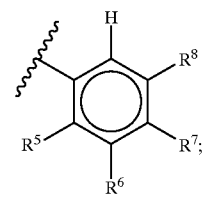

$R^2$ is phenyl of the formula $Ph^2$ or a five or six membered heteroctcle, wherein said 6-membered heterocycle has the formula

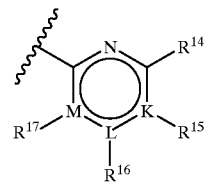

wherein "N" is nitrogen; wherein said ring positions "K", "L" and "M" may be independently selected from carbon or nitrogen, with the proviso that i) only one of "K", "L" or "M" can be nitrogen and ii) when "K", "L" or "M" is nitrogen then its respective $R^{15}$, $R^{16}$ or $R^{17}$ is absent;

wherein said five membered heterocycle has the formula

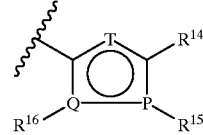

wherein said "T" is —CH—, N, NH, O or S; wherein said ring positions "P" and "Q" may be independently selected from carbon, nitrogen, oxygen or sulfur; with the proviso that only one of "P," "Q" or "T" can be oxygen or sulfur and at least one of "P," "Q" or "T" must be a heteroatom;

wherein said $Ph^2$ is a group of the formula

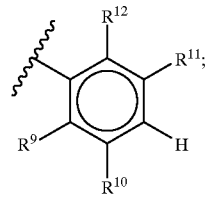

$R^3$ is fluoro or chloro;
$R^5$ is hydrogen, $(C_1-C_6)$alkyl, halo, $CF_3$, $(C_1-C_6)$alkoxy or $(C_1-C_6)$alkyl-S—;
$R^6$ is hydrogen or halo;
$R^7$ is hydrogen or halo;
$R^8$ is hydrogen or halo;
$R^9$ is hydrogen, halo, $CF_3$, $(C_1-C_6)$alkyl optionally substituted with one to three halogen atoms, $(C_1-C_6)$alkoxy optionally substituted with one to three halogen atoms, $(C_1-C_6)$alkyl-S—, amino-$(CH_2)_s$—, $(C_3-C_7)$alkyl-NH—$(CH_2)_s$—, di$(C_1-C_6)$alkyl-N—$(CH_2)_s$—, $(C_3-C_7)$cycloalkyl-NH—$(CH_2)_s$—, $H_2N$—(C=O)—$(CH_2)_s$—, $(C_1-C_6)$alkyl-HN—(C=O)—$(CH_2)_s$—, di$(C_1-C_6)$alkyl-N—(C=O)—$(CH_2)_s$—, $(C_3-C_7)$cycloalkyl-NH—(C=O)—$(CH_2)_s$—, $R^{13}O$—$(CH_2)_s$—, $R^{13}O$—(C=O)—$(CH_2)_s$—, H(O=C)—NH—$(CH_2)_s$—, $(C_1-C_6)$alkyl-(O=C)-NH—$(CH_2)_s$—, $(C_1-C_6)$alkyl-(O=C)—N(($C_1-C_6$)alkyl)$(CH_2)_s$—, H(O=C)—N(($C_1-C_6$)alkyl)$(CH_2)_s$—, H—(C=O)—$(CH_2)_s$—, $(C_1-C_6)$alkyl-(C=O)—, hydroxy, hydroxy-$(C_1-C_6)$alkyl $(C_1-C_6)$alkyl$(C_1-C_6)$alkyl-, $(C_1-C_6)$alkyl-O—$(C_1-C_6)$alkyl-, and —CN;

$R^{10}$ and $R^{14}$ are selected independently, from hydrogen, halo, $CF_3$, $(C_1-C_6)$alkyl optionally substituted with one to three halogen atoms, $(C_1-C_6)$alkoxy optionally substituted with one to three halogen atoms, $(C_1-C_6)$alkyl-S—, amino-$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, amino-$(C_1-C_6)$alkyl-NH—$(CH_2)_p$—, $(C_1-C_6)$alkyl-NH—$(C_1-C_6)$alkyl-NH—$(CH_2)_p$—, di$(C_1-C_6)$alkyl-N—$(C_1-C_6)$alkyl-NH—$(CH_2)_p$—, di$(C_1-C_6)$alkyl-N(($C_1-C_6$)alkyl)$(C_1-C_6)$alkyl-N—$(CH_2)_p$—, $H_2N$—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_3-C_7)$cycloalkyl-NH—(C=O)—$(CH_2)_p$—, $R^{13}O$—$(CH_2)_p$—, $R^{13}O$—(C=O)—$(CH_2)_p$—, H(O=C)—O—, H(O=C)—O—$(C_1-C_6)$alkyl-, H(O=C)—NH—$(CH_2)_p$—, $(C_1-C_6)$alkyl-(O=C)—NH—$(CH_2)_p$—, —CHO, H—(C=O)—$(CH_2)_p$—, $(C_1-C_6)$alkyl-(C=O)—$(CH_2)_p$—, $(C_1-C_6)$alkyl-(O=C)—N(($C_1-C_6$)alkyl)$(CH_2)_p$—, H(O=C)—N—(($C_1-C_6$)alkyl)$(CH_2)_p$—, HO—$(C_1-C_6)$alkyl-N(($C_1-C_6$)alkyl)$(CH_2)_p$—, $(C_1-C_6)$alkyl-(C=O)—O—NH—$(CH_2)_p$—, amino-$(C_1-C_6)$alkyl-(C=O)—C—$(CH_2)_p$—, $(C_1-C_6)$alkyl-NH—$(C_1-C_6)$alkyl-(C=O)—O—$(CH_2)_p$—, di$(C_1-C_6)$alkyl-N—$(C_1-C_6)$alkyl-(C=O)—O—$(CH_2)_p$—, amino-$(C_1-C_6)$alkyl-O—(C=O)—$(CH_2)_p$—, $(C_1-C_6)$alkyl-NH—$(C_1-C_6)$alkyl-O—(C=O)—$(CH_2)_p$—, di$(C_1-C_6)$alkyl-N—$(C_1-C_6)$alkyl-O—$(C=O)$—$(CH_2)_p$—, hydroxy, hydroxy-$(C_1-C_6)$alkyl-, hydroxy-$(C_1-C_6)$alkyl-NH—$(CH_2)_p$—, $(C_1-C_6)$alkyl-O—$(C_1-C_6)$alkyl-, —CN, piperidine-$(CH_2)_p$—, pyrrolidine-$(CH_2)_p$—, and 3-pyrroline-$(CH_2)_p$—, wherein said piperidine, pyrrolidine and 3-pyrroline of said piperidine-$(CH_2)_p$—, pyrrolidine-$(CH_2)_p$— and 3-pyrroline-$(CH_2)_p$— moieties may optionally be substituted on any of the ring carbon atoms capable of supporting and additional bond, with a substituent independently selected from halo, $CF_3$, $(C_1-C_6)$alkyl optionally substituted with one to three halogen atoms, $(C_1-C_6)$alkoxy optionally substituted with one to three halogen atoms, $(C_1-C_6)$alkyl-S—, amino-$(CH_2)_p$—, $(C_1-C_6)$alkyl-NH—$(CH_2)_p$—, di$(C_1-C_6)$alkyl-N—$(CH_2)_p$—, $(C_3-C_6)$cycloalkyl-NH—$(CH_2)_p$—, amino-$(C_1-C_6)$alkyl-NH—$(CH_2)_p$—, $(C_1-C_6)$alkyl-NH—$(C_1-C_6)$alkyl-NH—$(CH_2)_p$—, di$(C_1C_6)$alkyl-N—$(C_1-C_6)$alkyl-NH—$(CH_2)_p$—, $(C_1-C_6)$alkyl-O—$(C_1-C_6)$alkyl-, di$(C_1-C_6)$alkyl-N—$(C_1C_6)$alkyl-N(($C_1-C_6$)alkyl)$(CH_2)_p$—, $H_2N$—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$, $(C_3-C_7)$cycloalkyl-NH—(C=O)—$(CH_2)_p$—, $R^{13}O$—$(CH^2)_p$—, $R^{13}O$—(C=O)—$(CH_2)_p$—, H(O=C)—O—, H(O=C)—O—$(C_1-C_6)$alkyl-, H(O=C)—NH—$(CH_2)_p$—, $(C_1-C_6)$alkyl-(O=C)—NH—$(CH_2)_p$—, —CHO,
H—(C=O)—$(CH_2)_p$—, $(C_1-C_6)$alkyl-(C=O)—, $(C_1-C_6)$alkyl-(O=C)—N(($C_1-C_6$)alkyl)$(CH_2)_p$—, H(O=C)—N(($C_1-C_6$)alkyl)$(CH_2)_p$—, HO—$(C_1-C_6)$alkyl-N(($C_1-C_6$)alkyl)$(CH_2)_p$—, $(C_1-C_6)$alkyl-(C=O)—O—NH—$(CH_2)_p$—, amino-$(C_1-C_6)$alkyl-(C=O)—O—$(CH_2)_p$—, $(C_1-C_6)$alkyl-NH—$(C_1-C_6)$alkyl-(C=O)—O—$(CH_2)_p$—, di$(C_1-C_6)$alkyl-N—$(C_1-C_6)$alkyl-(C=O)—O—$(CH_2)_p$—, hydroxy, hydroxy-$(C_1-C_6)$alkyl-, hydroxy-$(C_1-C_6)$alkyl-NH—$(CH_2)_p$—, and —CN;

$R^{11}$ is hydrogen or halo;

$R^{12}$ is hydrogen, —CN or halo;

$R^{13}$ is hydrogen, $(C_1-C_6)$alkyl, $(C_1-C_6)$alkyl-(C=O)—, $(C_1-C_6)$alkyl-O—(C=O)—, $(C_1-C_6)$alkyl-NH—(C=O)—, or di$(C_1-C_6)$alkyl-N—(C=O)—;

$R^{15}$ is hydrogen, —CN, $(C_1-C_6)$alkyl, halo, $CF_3$, —CHO or $(C_1-C_6)$ alkoxy;

$R^{16}$ is hydrogen, —CN, $(C_1-C_6)$alkyl, halo, $CF_3$, —CHO or $(C_1-C_6)$alkoxy;

$R^{17}$ is hydrogen, —CN, $(C_1-C_6)$alkyl, amino-$(C_1-C_6)$alkyl-, $(C_1-C_6)$alkyl-NH—$(C_1-C_6)$alkyl-, di$(C_1-C_6)$alkyl-N—$(C_1-C_6)$alkyl-, halo, $CF_3$, —CHO or $(C_1-C_6)$alkoxy;

n is an integer from zero to 3;

each p is independently an integer from zero to 4;

s is an integer from zero to 4;

wherein the dashed bond represented an optional double bond;

with the proviso that: i) when $R^9$ is hydrogen, one of $R^{11}$ and $R^{12}$ is other than hydrogen; and ii) when $R^3$ is chloro; $R^5$ is methyl; $R^6$, $R^7$, and $R^8$ are hydrogen; and K, L and M equal carbon, then (a) one of $R^{14}$ through $R^{17}$ must be other than hydrogen or (b) $R^{17}$ must be other than hydrogen or methyl;

and the pharmaceutically acceptable salts of such compounds.

2. A compound according to claim 1 wherein $R^3$ is fluoro.

3. A compound according to claim 1 wherein $R^1$ is $Ph^1$ and one of $R^5$, $R^6$, $R^7$ or $R^8$ is fluoro, bromo, chloro, methyl or triluoromethyl.

4. A compound according to claim 1 wherein $R^1$ is $Ph^1$ and $R^5$ is fluoro, bromo, chloro, methyl or trifluoromethyl.

5. A compound according to claim 2 wherein $R^1$ is $Ph^1$ and $R^5$ is fluoro, bromo, chloro, methyl or trifluoromethyl.

6. A compound according to claim 1 wherein $R^2$ is $Ph^2$ and either $R^9$ is fluoro, chloro, —CN or hydroxy, or $R^{10}$ is —CHO, chloro, fluoro, methyl, $(C_1-C_6)$alkyl-NH—$(CH_2)_p$—, di$(C_1-C_6)$alkyl-N—$(CH_2)_p$—, or cyano.

7. A compound according to claim 2 wherein $R^2$ is $Ph^2$ and either $R^9$ is fluoro, chloro, —CN or hydroxy, or $R^{10}$ is —CHO, chloro, fluoro, methyl, $(C_1-C_6)$alkyl-NH—$(CH_2)_p$—, di$(C_1-C_6)$alkyl-N—$(CH_2)_p$—, or cyano.

8. A compound according to claim 1 wherein $R^1$ is heteroaryl optionally substituted with halo, —CN, $CF_3$, or $(C_1-C_6)$alkyl.

9. A compound according to claim 2 wherein $R^1$ is heteroaryl optionally substituted with halo, —CN, $CF_3$, or $(C_1-C_6)$alkyl.

10. A compound according to claim 6 wherein $R^1$ is heteroaryl optionally substituted with halo, —CN, $CF_3$, or $(C_1-C_6)$alkyl.

11. A compound according to claim 1 wherein $R^1$ is pyridin-3-yl optionally substituted with chloro or methyl.

12. A compound according to claim 1 wherein $R^1$ is pyridin-3-yl substituted at the 2-position of the pyridine ring with chloro or methyl.

13. A compound according to claim 1 wherein $R^2$ is heteroaryl are those wherein said heteroaryl is either an optionally substituted six-membered heterocycle wherein "K", "L" and "M" are carbon, or "K" and "L" are carbon and "M" is nitrogen (i.e. pyrimidin-2-yl), or said heteroaryl is an optionally substituted five membered heterocycle wherein "T" is nitrogen, "P" is sulfur and "Q" is carbon, or "T" is nitrogen or sulfur, "Q" is nitrogen or sulfur and "P" is carbon or "T" is oxygen and "P" and "Q" are each carbon.

14. A compound according to claim 1 wherein $R^2$ is an optionally substituted six-membered heterocycle wherein "K", "L" and "M" are carbon are those wherein $R^{14}$ is hydrogen, —CHO, chloro, fluoro, methyl, $(C_1-C_6)$alkyl-NH—$(CH_2)_p$—, di$(C_1-C_e)$alkyl-N—$(CH_2)_p$—, or cyano; $R^{17}$ is hydrogen, —CHO, chloro, fluoro, methyl, $(C_1-C_6)$ alkyl-NH—$(C_1-C_6)$alkyl, di$(C_1-C_6)$alkyl-N—$(C_1-C_6)$ alkyl, or cyano; or $R^{15}$ or $R^{16}$ are independently hydrogen, —CHO, chloro, fluoro, methyl or cyano.

15. A compound according to claim 1 wherein $R^2$ is an optionally substituted six-membered heterocycle wherein "K", "L" and "M" are carbon and $R^{14}$ is hydrogen, —CHO, methyl, $(C_1-C_6)$alkyl-NH—$(CH_2)_p$—, di$(C_1-C_6)$alkyl-N—$(CH_2)_p$—, or cyano.

16. A compound according to claim 1 wherein $R^2$ is an optionally substituted five-membered heterocycle wherein "T" is nitrogen, "P" is sulfur and "Q" is carbon and $R^{14}$, $R^{15}$ or $R^{16}$ are each independently hydrogen, chloro, fluoro, methyl or cyano.

17. A compound according to claim 1 wherein $R^2$ is an optionally substituted five-membered heterocycle wherein "T" is nitrogen or sulfur, "Q" is sulfur or nitrogen and "P" is carbon and $R^{14}$ or $R^{15}$ are independently selected from hydrogen, chloro, fluoro, methyl or cyano, with the proviso that only one of "Q" or "T" can be oxygen or sulfur.

18. A compound according to claim 1 wherein said compound is selected from the group consisting of:

3-(2-chloro-phenyl)-2-[2-(5-diethylaminomethyl-2-fluoro-phenyl)-vinyl]-6-fluoro-3H-quinazolin-4-one;

3-(2-chloro-phenyl)-2-[2-(6-diethylaminomethyl-pyridin-2-yl)-vinyl]-6-fluoro-3H-quinazolin-4-one;

3-(2-chloro-phenyl)-2-[2-(4-diethylaminomethyl-pyridin-2-yl)-vinyl]-6-fluoro-3H-quinazolin-4-one;

3-(2-chloro-phenyl)-2-[2-(6-ethylaminomethyl-pyridin-2-yl)-vinyl]-6-fluoro-3H-quinazolin-4-one;

3-(2-bromo-phenyl)-2-[2-(6-diethylaminomethyl-pyridin-2-yl)-vinyl]-6-fluoro-3H-quinazolin-4-one;

3-(2-chloro-phenyl)-6-fluoro-2-[2-(6-methoxymethyl-pyridin-2-yl)-vinyl]-3H-quinazolin-4-one;

6-fluoro-3-(2-methyl-pyridin-3-yl)-2-[2-(2-methyl-thiazol-4-yl)-vinyl]-3H-quinazolin-4-one;

3-(2-chloro-phenyl)-6-fluoro-2-[2-(4methyl-pyrimidine-2-yl)-vinyl]-3H-quinazolin-4-one;

3-(2-chloro-phenyl)-6-fluoro-2-{2-[6-(isopropylamino-methyl)-pyridin-2-yl]-ethyl}-3H-quinazolin-4-one; and 2-[2-(5-diethylaminomethyl-2-fluoro-phenyl)-vinyl]-6-fluoro3-(2-methyl-pyridin-3-yl)-3H-quinazolin-4-one.

19. A pharmaceutical composition for treating or preventing convulsions in a mammal, comprising an amount of a compound according to claim 1 effective in treating or preventing convulsions and a pharmaceutically acceptable carrier.

20. A method for treating or preventing in a mammal, comprising administering to a mammal requiring such treatment or prevention an amount of a compound according to claim 1 effective in treating or preventing convulsions.

* * * * *